US008715675B2

(12) United States Patent
Schnitzer et al.

(10) Patent No.: US 8,715,675 B2
(45) Date of Patent: May 6, 2014

(54) VASCULAR TARGETS FOR DETECTING, IMAGING AND TREATING NEOPLASIA OR NEOVASCULATURE

(75) Inventors: Jan E. Schnitzer, Encinitas, CA (US); Philip Oh, San Diego, CA (US)

(73) Assignee: Jan E. Schnitzer, San Diego, CA (US)

( * ) Notice: Subject to any disclaimer, the term of this patent is extended or adjusted under 35 U.S.C. 154(b) by 58 days.

(21) Appl. No.: 12/766,062

(22) Filed: Apr. 23, 2010

(65) Prior Publication Data

US 2011/0044893 A1 Feb. 24, 2011

Related U.S. Application Data

(63) Continuation of application No. 11/143,886, filed on Jun. 2, 2005, now abandoned.

(60) Provisional application No. 60/576,116, filed on Jun. 2, 2004.

(51) Int. Cl.
*A61K 39/395* (2006.01)

(52) U.S. Cl.
USPC .................................. 424/178.1; 424/174.1

(58) Field of Classification Search
None
See application file for complete search history.

(56) References Cited

U.S. PATENT DOCUMENTS

| | | | | |
|---|---|---|---|---|
| 4,331,647 | A * | 5/1982 | Goldenberg | ................. 424/1.37 |
| 5,314,992 | A | 5/1994 | Guyre et al. | |
| 5,658,877 | A | 8/1997 | Tsao | |
| 5,855,866 | A | 1/1999 | Thorpe et al. | |
| 6,180,596 | B1 | 1/2001 | Tsao | |
| 6,261,535 | B1 | 7/2001 | Thorpe et al. | |
| 6,312,694 | B1 | 11/2001 | Thorpe et al. | |
| 7,125,541 | B2 | 10/2006 | Thorpe et al. | |
| 7,182,933 | B2 | 2/2007 | Goetz et al. | |
| 2002/0151470 | A1 | 10/2002 | Patierno et al. | |
| 2003/0008819 | A1 | 1/2003 | Schnitzer et al. | |
| 2003/0162706 | A1 | 8/2003 | Peters et al. | |
| 2003/0232762 | A1 | 12/2003 | Ruoslahti et al. | |
| 2006/0024232 | A1 | 2/2006 | Schnitzer et al. | |

FOREIGN PATENT DOCUMENTS

| | | |
|---|---|---|
| DE | 100 17 249 A1 | 10/2001 |
| WO | 9709055 | 3/1997 |
| WO | WO 98/53852 | 12/1998 |
| WO | WO 99/13329 | 3/1999 |
| WO | WO 99/21980 | 5/1999 |
| WO | 0002584 | 1/2000 |
| WO | 0052467 | 9/2000 |
| WO | WO 00/78361 A2 | 12/2000 |
| WO | WO 01/10461 A1 | 2/2001 |
| WO | WO 02/30473 A1 | 4/2002 |
| WO | 02082044 | 10/2002 |
| WO | WO 02/076394 A2 | 10/2002 |
| WO | WO 2004/098535 A2 | 11/2004 |
| WO | WO 2005/012489 A2 | 2/2005 |
| WO | WO 2005/019429 A2 | 3/2005 |
| WO | WO 2005/027965 A1 | 3/2005 |
| WO | WO 2005/046573 A2 | 5/2005 |
| WO | WO 2005/094882 A1 | 10/2005 |

OTHER PUBLICATIONS

Bai, Xiao-Geng, et al., "Overexpression of annexin 1 in pancreatic cancer and its clinical significance," *World J Gastroenterol.*, 10(10): 1466-1470 (2004).
Kang, J. S., et al., "Dysregulation of Annexin I Protein Expression in High-Grade Prostatic Intraepithelial Neoplasia and Prostate Cancer," *Clinical Cancer Research*, 8: 117-123 (Jan. 2002).
Pedrero, J. M. G., et al., "Annexin A1 Down-Regulation in Head and Neck Cancer is Associated with Epithelial Differentiation Status," *American Journal of Pathology*, 164(1): 73-79 (Jan. 2004).
Taiwan Search Report and Examination Report completed on May 4, 2011 from Taiwan Application No. 94118131, filed Jun. 2, 2005 (English Translation).
McKanna, J. A. and Zhang, M., "Immunohistochemical Localization of Lipocortin 1 in Rat Brain is Sensitive to pH, Freezing, and Dehydration," *J. Histochem. & Cytochem.*, 45 (4): 527-538 (1997).
Savchenko, V. L., et al., "Microglia and Astrocytes in the Adult Rat Brain: Comparative Immunocytochemical Analysis Demonstrates the Efficacy of Lipocortin 1 Immunoreactivity," *Neurosci.*, 96(1): 195-203 (2000).
Eberhard, D. A., et al., "Alterations of Annexin Expression in Pathological Neuronal and Glial Reactions," *Am. J. of Pathology*, 145(3): 640-649 (1994).
Dreier, R., et al., "Differential Expression of Annexins I, II and IV in Human Tissues: an Immunohistochemical Study," *Histochem Cell Biol.*, 110(2): 137-148 (1998).
Pencil, S. D. and Toth, M., "Elevated Levels of Annexin I Protein in vitro and in vivo in Rat and Human Mammary Adenocarcinoma," *Clin. Exp. Metastasis*, 16(2): 113-121 (1998).
Ahn, S., et al. "Differential Expression of Annexin I in Human Mammary Ductal Epithelial Cells in Normal and Benign and Malignant Breast Tissues," *Clin. Exp. Metastasis*, 15(2): 151-156 (1997).
Anzick, S. L., et al. "Role of Genomics in Identifying New Targets for Cancer Therapy," *Onocology, Suppl. No. 4*, 16(5): 7-13 (2002).
Dvorak, H. F., et al., "Structure of Solid Tumors and Their Vasculature: Implications for Therapy With Monoclonal Antibodies," *Cancer Cells*, 3(2): 77-85 (1991).
Schwartz-Albiez, R., et al., "Differential Expression of Annexins I and II in Normal and Malignant Human Mammary Epithelial Cells," *Differentiation*, 52: 229-237 (1993).
Gerke, V. And Moss, S. E., "Annexins: From Structure to Function," *Am. Physiol. Soc.*, 82: 331-371 (2002).
Traverso, V., et al., "Lipocortin 1 (annexin 1) in Patches Associated With the Membrane of a Lung Adenocarcinoma Cell Line and in the Cell Cytoplasm," *J. Cell Sci.*, 111: 1405-1418 (1998).

(Continued)

*Primary Examiner* — Mark Halvorson
(74) *Attorney, Agent, or Firm* — Hamilton, Brook, Smith & Reynolds, P.C.

(57) ABSTRACT

Methods of delivering an agent in a tissue-specific manner, by targeting annexin A1, a derivative of annexin A1, or a binding partner of annexin A1, are described. The methods can be used for detecting, imaging and/or treating neoplasia, angiogenesis or neovasculature, as well as for diagnostics and methods of assessing treatment efficacy. Antibodies to annexin A1 are also described, as are methods screening for agents altering annexin A1 activity.

6 Claims, 1 Drawing Sheet

(56) References Cited

OTHER PUBLICATIONS

Guzmán-Aránguez, A., et al., "Differentiation of Human Colon Adenocarcinoma Cells Alters the Expression and Intracellular Localization of Annexins A1, A2 and A5," *J. Of Cell. Biochem.*, 94: 178-193 (2005).
Naciff, J. M., et al., "Differential Expression of Annexins I-VI in the Rat Dorsal Root Ganglia and Spinal Cord," *J. Compar. Neurol.*, 368: 356-370 (1996).
Shen, D., et al., "Loss of Annexin A1 Expression in Human Breast Cancer Detected by Multiple High-Throughput Analyses," *Biochem. and Biophys. Research Comm.*, 326: 218-227 (2005).
Carver, L. A. and Schnitzer, J. E., "Caveolae: Mining Little Caves for New Cancer Targets," *Nature*, 3: 571-581 (2003).
McIntosh, D. P. And Schnitzer, J. E., "Caveolae Require Intact VAMP For Targeted Transport in Vascular Endothelium," *Am. Physio. Soc.*, H222-H2232 (1999).
Schnitzer, J. E., et al., "NEM Inhibits Transcytosis, Endocytosis and Capillary Permeability: Implication of Caveolae Fusion in Endothelia," *Am. Physio. Soc.*, H48-H55 (1995).
Schnitzer, J. E., et al., "Endothelial Caveolae Have the Molecular Transport Machinery For Vesicle Budding, Docking, and Fusion Including VAMP, NSF, SNAP, Annexins, and GTPases," *J. Biol. Chem.*, 270(24): 14399-14404 (1996).
Schnitzer, J. E., et al., "Filipin-Sensitive Caveolae-Mediated Transport in Endothelium: Reduced Transcytosis, Scavenger Endocytosis, and Capillary Permeability of Select Macromolecules," *J. Cell Biol.*, 127(5): 1217-1232 (1994).
Schnitzer, J. E., "Caveolae: From Basic Trafficking Mechanisms to Targeting Transcytosis for Tissue-Specific Drug and Gene Delivery in vivo," *Adv. Drug Deliv. Rev.*, 49: 265-280 (2001).
Schnitzer, J. E. and Oh, Phil, "Albondin-Mediated Capillary Permeability to Albumin," *J. Biol. Chem.*, 269(8): 6072-6082 (1994).
Schnitzer, J. E., et al., "Separation of Caveolae From Associated Microdomains of GPI-Anchored Proteins," *Science*, 269: 1435-1439 (1995).
Schnitzer, J. E., et al., "Role of GTP Hydrolysis in Fission of Caveolae Directly From Plasma Membranes," *Science*, 274: 239-242 (1996).
Contag, C. H. and Bachmann, M. H., "The Writing is on the Vessel Wall," *Nature*, 429: 618-619 (2004).
Oh, P., et al., "Subtractive Proteomic Mapping of the Endothelial Surface in Lung and Solid Tumours for Tissue-Specific Therapy," *Nature*, 429: 629-635 (2004).
Brichory, F. M., et al., "An Immune Response Manifested by the Common Occurrence of Annexins I and II Autoantibodies and High Circulating Levels of IL-6 in Lung Cancer," *Proc. Natl. Acad. Sci.*,, 98(17): 9824-9829 (2001).
McIntosh, D. P., et al., "Targeting Endothelium and its Dynamic Cavcolac for Tissue-Specific Transcytosis in vivo: A Pathway to Overcome Cell Barriers to Drug and Gene Delivery," *Proc. Natl. Acad. Sci.*,, 99(4): 1996-2001 (2002).
Drews, J., "Drug Discovery: A Historical Perspective," *Science*, 287: 1960-1964 (2000).
Lindsay, M. A., "Target Discovery," *Nature Rev.*, 2: 831-838 (2003).
Workman, P., "New Drug Targets for Genomic Cancer Therapy: Successes, Limitations, Opportunities and Future Challenges," *Curr. Cancer Drug Targets*, pp. 33-47 (2001).
Cavenee, W. K., "Genetics and New Approaches to Cancer Therapy," *Carcinogen.*, 28(5): 683-686 (2002).
Huber, L. A., "Is Proteomics Heading in the Wrong Direction?," *Nature Rev.*, 4: 74-80 (2003).
Perou, C. M., et al., "Molecular Portraits of Human Breast Tumors," *Nature*, 406: 747-752 (2000).
Jain, R. K., "The Next Frontier of Molecular Medicine: Delivery of Therapeutics," *Nature Med.*, 4(6): 655-657 (1998).
Massoud, T. F. and Gambhir, S. S., "Molecular Imaging in Living Subjects: Seeing Fundamental Biological Processes in a New Light," *Genes & Devel.*, 17: 545-580 (2003).
Herschman, H. R., "Molecular Imaging: Looking at Problems, Seeing Solutions," *Science*, 302: 605-608 (2003).
Rudin, M. And Weissleder, R., "Molecular Imaging in Drug Discovery and Development," *Nature Rev.*, 2: 123-131 (2003).
Weissleder, R., "Scaling Down Imaging: Molecular Mapping of Cancer in Mice," *Nature Rev.* 2: 1-8 (2001).
Pasqualini, R. and Ruoslahti, E., "Organ Targeting in vivo Using Phage Display Peptide Libraries," *Nature*, 380: 364-366 (1996).
Muzykantov, V. R., et al., "Immunotargeting of Antioxidant Enzymes to the Pulmonary Endothelium," *Proc. Natl. Acad. Sci.*, 93: pp. 5213-5218 (1996).
Muzykantov, V. R., et al., "Streptavidin Facilitates Internalization and Pulmonary Targeting of an Anti-Endothelial Cell Antibody (platelet-endothelial cell adhesion molecule 1): A Strategy for Vascular Immunotargeting of Drugs," *Proc. Natl. Acad. Sci.*, 96: pp. 2379-2384 (1999).
Schnitzer, J. E., "Update on the Cellular and Molecular Basis of Capillary Permeability," *TCM*, 3(4): 124-130 (1993).
Essler, M. et al., "Molecular Specialization of Breast Vasculature: A Breast-Homing Phage-Displayed Peptide Binds to Aminopeptidase P in Breast Vasculature," *Proc. Natl. Acad. Sci.*, 99: pp. 2252-2257 (2002).
Ruoslahti, E., "Drug Targeting to Specific Vascular Sites," *Drug Discovery Today*, 7: 1138-1143 (2002).
Durr, E., et al., "Direct Proteomic Mapping of the Lung Microvascular Endothelial Cell Surface in Vivo and In Cell Culture," *Nature Biotechnology*, 22: 985-992 (2004).
Falini, B., et al., "Simple Diagnostic Assay for Hairy Cell Leukaemia in Immunocytochemical Dection of *annexin* A1 (ANXA1)," *Lancet* 363: 1869-1871 (2004).
Hayes, M. J. and Moss, S.E., "Annexins and Disease," *Biochemical and Biophysical Research Communications*, 322: 1166-1170 (2004).
Kraus, M. et al., "Detection of Human Anti-Annexin Autoantibodies by Enzyme Immunoassays," *Journal of Immunoassay*, 13: 411-439 (1992).
Wang, Y., et al., "Annexin-I Expression Modulates Drug Resistance in Tumor Cells," *Biochemical and Biophysical Research Communications*, 314: 565-570 (2004).
Croxtall, J. D., et al., "N-Terminal Peptide Fragments of Lipocortin-1 Inhibit A549 Cell Growth and Block EGF-Induced Stimulation of Proliferation," *International Journal of Cancer*, 54: 153-157 (1993).
Park, J. E., et al., "Annexin A3 is a Potential Angiogenic Mediator," *Biochemical and Biophysical Research Communications*, 337: 1283-1287 (2005).
Lim, L. H., et al., "Promoting Detachment of Neutrophils Adherent to Murine Postcapillary Venules to Control Inflammation Effect of Lipocortin 1," *Proceedings of the National Academy of Sciences of USA*, 95: 14535-14539 (1998).
Gavins, F. N. E., et al., "A Twist in Anti-Inflammation: Annexin 1 Acts Via the Lipoxin A4 Receptor," *Prostaglandins Leukotrienes and Essential Fatty Acids*, 73: 211-219 (2005).
Carver, L. A., and J.E. Schnitzer, "Caveolae: Mining Little Caves for New Cancer Targets," *Nature Reviews*, 3:571-581 (2003).
Christian, S., et al., "Nucleolin Expressed at the Cell Surface is a Marker of Endothelial Cells in Angiogenic Blood Vessels," *Journal of Cell Biology*, 163:871-878 (2003).
Van Hensbergen, Y., et al., "A Doxorubicin-CNGRC-Peptide Conjugate with Prodrug Properties," *Biochemical Pharmacology*, 63:897-908 (2002).
Pastorino, F., et al., "Vascular Damage and Anti-Angiogenic Effects of Tumor Vessel-Targeted Liposomal Chemotherapy," *Cancer Research*, 63:7400-7409 (2003).
Arap, W., et al., "Cancer Treatment by Targeted Drug Delivery to Tumor Vasculature in a Mouse Model," *Science*, 279:377-380 (1998).
Oh, P., et al., "Mapping and Targeting Proteins at the Endothelial Cell Surface and Its Caveolae for Improved Penetration, Imaging and Radiodestruction of Solid Tumors," *Eur. Jour. of Cancer Supp.*, 2:4 (2004).
De Coupade, C., et al., "Annexin 1 Expression and Phosphorylation Are Upregulated During Liver Regeneration and Transformation in Antithrombin III SV40 T Large Antigen Transgenic Mice," *Hepatalogy*, p. 371-380 (Feb. 2000).
Silistano-Souza, R., et al., "Annexin 1: Differential Expression in Tumor and Mast Cells in Human Larynx Cancer," Int. J. Cancer: 120, 2582-2589 (Mar. 2007).
Office Action dated Mar. 13, 2013 for U.S. Appl. No. 11/143,919.

\* cited by examiner

US 8,715,675 B2

VASCULAR TARGETS FOR DETECTING, IMAGING AND TREATING NEOPLASIA OR NEOVASCULATURE

RELATED APPLICATIONS

This application is a continuation of U.S. application Ser. No. 11/143,886, filed Jun. 2, 2005 now abandoned, which claims the benefit of U.S. Provisional Application No. 60/576,116, filed Jun. 2, 2004. The entire teachings of the above applications are incorporated herein by reference.

GOVERNMENT SUPPORT

The invention was supported, in whole or in part, by grant 1 R33 CA97528-01 and grant 1 R01 CA83989-01A2 from the National Institute of Health (NIH). The Government has certain rights in the invention.

BACKGROUND OF THE INVENTION

Selectively targeting solid tumors in vivo is a highly desirable but so far elusive goal for cancer therapy (Dvorak, H. F., et al., (1991) Cancer Cells 3, 77-85; Auerbach, R. (1991) Int J Radiat Biol 60, 1-10; Burrows, F. J. and Thorpe, P. E. (1994) Pharmacol Ther 64, 155-74; Schnitzer, J. E. (1998) N Engl J Med 339, 472-4). Current therapies for solid tumors lack sufficient tumor-specific targeting to avoid systemic side effects (Burrows, F. J. and Thorpe, P. E. (1994) Pharmacol Ther 64, 155-74; Schnitzer, J. E. (1998) N Engl J Med 339, 472-4; Schnitzer, J. E. (2001) Adv Drug Deliv Rev 49, 265-80). Pharmaceuticals conjugated to tumor-cell specific antibodies may show excellent specific activity in vitro; however, when injected intravenously as "magic bullets" to target neoplastic cells inside the tumor tissue they encounter significant barriers in vivo that limit accessibility and reduce bioavailability and bioefficacy (Dvorak, H. F., et al., (1991) Cancer Cells 3, 77-85).

SUMMARY OF THE INVENTION

The present invention pertains to methods of delivering agents to, into and/or across vascular endothelium in a neoplasm-specific manner. In the methods of the invention, the agent is delivered by contacting the luminal surface of vasculature, or caveolae of the vasculature, with an agent that specifically binds to annexin A1, to a derivative of annexin A1, to a specific binding partner of annexin A1, or to a specific binding partner of a derivative of annexin A1; alternatively, the agent is delivered by contacting the luminal surface of the vasculature, or caveolae of the vasculature, with annexin A1 or a derivative of annexin A1.

In certain embodiments of the invention, the methods can be used for treating neoplasia in an individual, by administering to the individual an annexin A1 therapeutic agent. The annnexin A1 therapeutic agent can be an antibody to annexin A1 or to a derivative of annexin A1; alternatively, the annexin A1 therapeutic agent can be annexin A1 receptor or an annexin A1 binding agent. In addition, the annexin A1 therapeutic agent can also be an agent having an active agent component and a targeting agent component, in which the targeting agent component is: an agent that specifically binds to annexin A1 or to a derivative of annexin A1 (e.g., an antibody to annexin A1 or to a derivative of annexin A1); annexin A1 or a derivative of Annexin A1; a specific binding partner of annexin A1 or a specific binding partner of a derivative of annexin A1; or an agent that binds to a specific binding partner of annexin A1 or to a specific binding partner of a derivative of annexin A1. In these embodiments, the active agent component can be, for example, a radionuclide; a chemotherapeutic agent; an immune stimulatory agent; an antineoplastic agent: an anti-inflammatory agent; a pro-apoptotic agent; a pro-coagulant; a toxin; an antibiotic; a hormone; an enzyme; a protein (e.g., a recombinant protein or a recombinant modified protein) a carrier protein (e.g., albumin, modified albumin); a lytic agent; a small molecule; aptamers; cells, including modified cells; vaccine-induced or other immune cells; nanoparticles (e.g., albumin-based nanoparticles); transferrins; immunoglobulins; multivalent antibodies; lipids; lipoproteins; liposomes; an altered natural ligand; a gene or nucleic acid; RNA; siRNA; a viral or non-viral gene delivery vector; a prodrug; or a promolecule. The invention additionally pertains to physiological compositions incorporating an annexin A1 therapeutic agent.

The invention also pertains to methods of assessing response to treatment with an annexin A1 therapeutic agent, by assessing the level of annexin A1 in a sample from the individual before treatment with an annexin A1 therapeutic agent, and during or after treatment with the annexin A1 therapeutic agent, and comparing the levels; a level of annexin A1 during or after treatment that is significantly lower than the level of annexin A1 before treatment, is indicative of efficacy of treatment with the annexin A1 therapeutic agent.

The invention further pertains to methods for performing physical imaging of an individual, using an imaging agent that includes a targeting agent component (as described above) and an imaging agent component. The imaging agent component can be, for example, a radioactive agent, radioisotope or radiopharmaceutical; a contrast agent; a magnetic agent or a paramagnetic agent; liposomes; ultrasound agents; nanoparticles; a gene vector or virus inducing a detecting agent; an enzyme; a prosthetic group; a fluorescent material; a luminescent material; or a bioluminescent material. Upon administration, the targeted imaging agents can be visualized noninvasively by conventional external detection means (designed for the imaging agent), to detect the preferential or specific accumulation in the neoplasm. In addition, the invention pertains to methods of delivering such imaging agents in vivo in a neoplasm-specific manner, and then assessing a biopsy sample for the presence of the imaging agent; the methods also pertain to delivering imaging agents in a neoplasm-specific manner to a tissue sample. The methods additionally pertain to methods assessing an individual for the presence or absence of a neoplasm, administering to the individual an agent of interest that comprises an imaging agent component and a targeting agent component, as described above, and assessing the individual for the presence or absence of a concentration of the agent of interest, wherein the presence of a concentration of the agent of interest is indicative of the presence of a neoplasm.

The present invention additionally pertains to methods of delivering agents to, into and/or across vascular endothelium in a neovasculature-specific manner. In the methods of the invention, the agent is delivered by contacting the luminal surface of vasculature with an agent that specifically binds to annexin A1, to a derivative of annexin A1, to a specific binding partner of annexin A1, or to a specific binding partner of a derivative of annexin A1; alternatively, the agent is delivered by contacting the luminal surface of the vasculature with annexin A1 or a derivative of annexin A1.

In certain embodiments of the invention, the methods can be used for treating treating neovasculature (e.g., angiogenesis, the development of undesirable neovasculature) in an individual, by administering to the individual an annexin A1 therapeutic agent. The annnexin A1 therapeutic agent can be an antibody to annexin A1 or to a derivative of annexin A1; alternatively, the annexin A1 therapeutic agent can be annexin A1 receptor or an annexin A1 binding agent. In addition, the annexin A1 therapeutic agent can also be an agent having an active agent component and a targeting agent component, in which the targeting agent component is: an agent that specifically binds to annexin A1 or to a derivative of annexin A1 (e.g., an antibody to annexin A1 or to a derivative of annexin A1); annexin A1 or a derivative of Annexin A1; a specific binding partner of annexin A1 or a specific binding partner of a derivative of annexin A1; or an agent that binds to a specific binding partner of annexin A1 or to a specific binding partner of a derivative of annexin A1. In these embodiments, the active agent component can be, for example, a radionuclide; a chemotherapeutic agent; an immune stimulatory agent; an anti-neoplastic agent: an anti-inflammatory agent; a pro-inflammatory agent; a pro-apoptotic agent; a pro-coagulant; toxin; an antibiotic; a hormone; a protein; a lytic agent; a small molecule; aptamers; cells; nanoparticles; lipids; lipoproteins; liposomes; an altered natural ligand; a gene or nucleic acid; a viral or non-viral gene delivery vector; a prodrug; or a promolecule.

In certain other embodiments of the invention, the methods can be used for enhancing or increasing neovasculature in an individual, by administering to the individual an annexin A1 neovasculature agent.

In addition, the invention pertains to methods of delivering such imaging agents in vivo in a neovasculature-specific manner, and then assessing a biopsy sample for the presence of the imaging agent; the methods also pertain to delivering imaging agents in a neovasculature-specific manner to a tissue sample. The methods additionally pertain to methods of assessing an individual for the presence or absence of neovasculature, administering to the individual an agent of interest that comprises an imaging agent component and a targeting agent component, as described above, and assessing the individual for the presence or absence of a concentration of the agent of interest, wherein the presence of a concentration of the agent of interest is indicative of the presence of neovasculature.

The invention additionally pertains to methods of identifying agents which alter activity of annexin A1 or an annexin A1 derivative, by assessing the level of activity of annexin A1 or annexin A1 derivative in the presence and in the absence of an agent to be tested, wherein if the level of activity of the annexin A1 or annexin A1 derivative in the presence of the agent differs, by an amount that is statistically significant, from the level of activity of the annexin A1 or annexin A1 derivative in the absence of the agent, then the agent is an agent that alters activity of the annexin A1 or annexin A1 derivative. Agents which alter activity of annexin A1 or an annexin A1 derivative, identifiable by these methods, are also contemplated by the invention.

BRIEF DESCRIPTION OF THE DRAWINGS

The foregoing and other objects, features and advantages of the invention will be apparent from the following more particular description of preferred embodiments of the invention, as illustrated in the accompanying drawing.

DETAILED DESCRIPTION OF THE INVENTION

Figure 1:
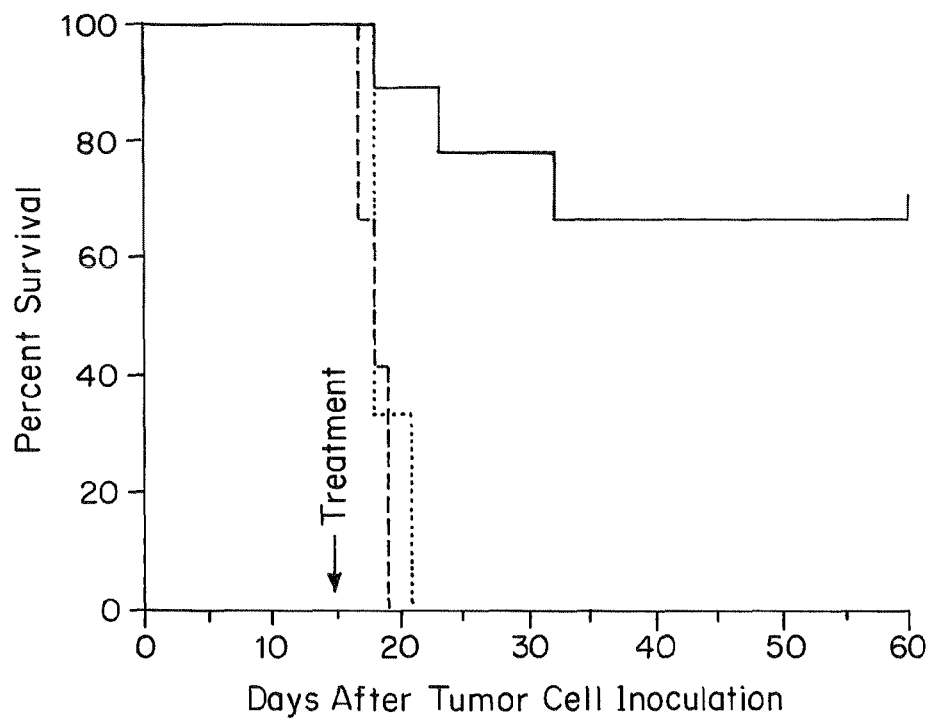
FIG. 1 depicts survival plotted on a Kaplan-Meier survival curve. Significantly increased survival of the tumor-bearing rats was observed, with 80% of the animals surviving 8 days or longer after injection compared to 100% mortality in the control rats by 7 days post-injection with AnnA1 antibodies.

A description of preferred embodiments of the invention follows. The invention is based on the discovery that solid tumors induce antibody accessible translocation of AnnA1 and derivatives of AnnA1 in caveolae of the neovasculature.

Vascular Endothelium and Tumor Accessibility

Plasmalemmal vesicles called caveolae are abundant on the endothelial cell surface, function in selective endocytosis and transcytosis of nutrients, and provide a means to enter endothelial cells (endocytosis) and/or to penetrate the endothelial cell barrier (transcytosis) for delivery to underlying tissue cells. Focus is now on the vascular endothelial cell surface in contact with the circulating blood, to bypass the problem of poor penetrability into tumors; this vascular endothelial cell surface provides an inherently accessible, and thus targetable, surface. Intravenously-accessible neovascular targets induced in tumors and not expressed or externalized in the endothelium of normal organs are useful for this strategy.

Past work has mapped and characterized extensively the molecular architecture and function of the cell surface and especially its caveolae in normal vascular endothelium, primarily in rat lung tissue (Schnitzer, J. E. and Oh, P. (1994) J Biol Chem 269, 6072-82; Schnitzer, J. E.,et al., (1994) J Cell Biol 127, 1217-32; Schnitzer, J. E., et al., (1995) Science 269, 1435-9; Schnitzer, J. E., et al., (1996) [publisher's erratum appears in Science 1996 Nov. 15 ;274(5290):1069]. Science 274, 239-42; Schnitzer, J. E., et al., (1995). J Biol Chem 270, 14399-404; Schnitzer, J. E., et al., (1995) Am J Physiol 268, H48-55; McIntosh, D. P. and Schnitzer, J. E. (1999) Am J Physiol 277, H2222-32). Investigation into the equivalence of these normal rat lung endothelial caveolae to endothelial caveolae from tumors and even human caveolae has begun. Normal rat lung endothelial caveolae contain annexin A2 (AnnA2) but not annexin A1 (AnnA1) which was thought to be restricted in expression to neuronal and select secretory cells (McKanna, J. A. and Zhang, M. Z. (1997. J Histochem Cytochem 45, 527-38; Savchenko, V. L. et al., (2000) Neuroscience 96, 195-203; Naciff, J. M., et al., (1996) J Comp Neurol 368, 356-70; Eberhard, D. A., et al., (1994) Am J Pathol 145, 640-9) Annexins including AnnA1 usually are cytosolic proteins that can bind lipid membranes in a calcium-dependent manner (Gerke, V., and Moss, S. E., Physiol Rev 2002; 82:331-71). When present at the cell surface, they usually exist bound at the inner leaflet of the bilayer but some annexins may be able to translocate across the lipid bilayer to remain bound to the plasma membrane at the external surface (Gerke, V. and Moss, S. E. (2002) Physiol Rev 82, 331-71).

Surprisingly, proteomic mapping of endothelium and its caveolae, as described in the Exemplification, revealed that solid tumors induce antibody accessible translocation of a 34 kDa-form of annexin A1 in caveolae of the neovasculature. Targeting tumor endothelial caveolae via annexin A1 permits specific delivery to, penetration into, imaging of, and destruction of solid tumors in vivo and in vitro. In addition, in view of the role of angiogenesis and development of neovasculature in development and maintenance of solid neoplasms, the targeting of endothelial caveolae via annexin A1 also permits specific delivery to, penetration into, imaging of, and destruction of neoplasms and neovasculature in vivo and in vitro. Furthermore, it allows use of the described agents for manufacture of medicaments for use in delivery to, treatment of, and/or imaging of neoplasms or neovasculature.

Methods of the Invention

As a result of this discovery, methods are now available to deliver agents to, into and/or across vascular endothelium in a neoplasm-specific manner, using annexin A1, a derivative of annexin A1, an agent that specifically binds to annexin A1 or to a derivative of annexin A1, or using an agent that specifically binds to a binding partner of annexin A1 or to a binding partner of a derivative of annexin A1. It is believed that delivery to, into, and/or across vascular endothelium of a neoplasm can allow delivery of agents into the interstitium of a neoplasm, allowing an agent to be delivered to all areas of a neoplasm (including endothelial, stromal, and other parts of a tumor). Similarly, a result of this discovery, methods are now available to deliver agents to, into and/or across vascular endothelium in a neovasculature-specific manner, using annexin A1, a derivative of annexin A1, an agent that specifically binds to annexin A1 or to a derivative of annexin A1, or using an agent that specifically binds to a binding partner of annexin A1 or to a binding partner of a derivative of annexin A1. It is believed that delivery to, into, and/or across vascular endothelium can allow an agent to be delivered to areas comprising neovasculature.

In certain embodiments of the invention, the methods deliver an annexin A1 therapeutic agent to, into and/or across vascular endothelium in a neoplasm-specific manner. These methods can be used to treat neoplasias or other disease states in an individual. The term, "neoplasm," as used herein refers particularly to malignant neoplasms, and includes not only to sarcomas (e.g., fibrosarcoma, myosarcoma, liposarcoma, chondrosarcoma, hemangiosarcoma, mesothelioma, leukemias, lymphomas, leiomyo sarcoma, rhabdomyo sarcoma), but also to carcinomas (e.g., adenocarcinoma, papillary carcinoma, cystadenocarcinoma, melanoma, renal cell carcinoma, hepatoma, choriocarcinoma, seminoma), as well as mixed neoplasms (e.g., teratomas). Thus, "neoplasm" contemplates not only solid tumors, but also so-called "soft" tumors. Furthermore, "neoplasm" contemplates not only primary neoplasms, but also metastases. In representative embodiments, neoplasms that can be targeted include brain, breast, lung, kidney, prostate, ovarian, head and neck, and liver tumors. In other embodiments of the invention, the methods deliver an imaging agent to, into and/or across vascular endothelium in a neoplasm-specific manner.

In certain other embodiments of the invention, the methods deliver an annexin A1 therapeutic agent to, into and/or across vascular endothelium in a neovasculature-specific manner. These methods can be used to treat undesirable neovasculature or other disease states in an individual. In other embodiments of the invention, the methods deliver an imaging agent to, into and/or across vascular endothelium in a neovasculature-specific manner. In further embodiments of the invention, the methods deliver an annexin A1 therapeutic agent to, into and/or across vascular endothelium in a neovasculature-specific manner in order to enhance or increase neovasculature if desired. Also available are in vivo and ex vivo diagnostics, utilizing an agent that specifically binds to annexin A1 or to a derivative of annexin A1, including methods to assess treatment efficacy as well as to assess prognosis of disease. Screening methods to identify agents altering activity of annexin A1 are also described, as are antibodies to annexin A1, which can be used in the methods of the invention.

A "derivative" of annexin A1, as the term is used herein, refers to a variant annexin A1 polypeptide which shares significant homology with annexin A1 (e.g., with human annexin A1, rat annexin A1, bovine annexin A1). Derivatives can encompass fragments and/or sequence variants. Variants include a substantially homologous polypeptide encoded by the same genetic locus in an organism, i.e., an allelic variant, as well as other splicing variants. Variants also encompass polypeptides derived from other genetic loci in an organism, but having substantial homology to annexin A1. Variants also include polypeptides substantially homologous or identical to these polypeptides but derived from another organism, i.e., an ortholog. Variants also include polypeptides that are substantially homologous or identical to these polypeptides that are produced by chemical synthesis. Variants also include polypeptides that are substantially homologous or identical to these polypeptides that are produced by recombinant methods.

As used herein, two polypeptides (or a region of the polypeptides) are substantially homologous or identical when the amino acid sequences are at least about 45-55%, typically at least about 70-75%, more typically at least about 80-85%, and most typically greater than about 90% or more homologous or identical. To determine the percent homology or identity of two amino acid sequences, or of two nucleic acid sequences, the sequences are aligned for optimal comparison purposes (e.g., gaps can be introduced in the sequence of one polypeptide or nucleic acid molecule for optimal alignment with the other polypeptide or nucleic acid molecule). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

The invention also encompasses derivative polypeptides having a lower degree of identity but having sufficient similarity so as to perform one or more of the same functions performed by annexin A1, such as a derivative having substitutions that conservatively replace a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found in Bowie et al., Science 247:1306-1310 (1990).

A derivative annexin A1 polypeptide can differ in amino acid sequence by one or more substitutions, deletions, insertions, inversions, fusions, and truncations or a combination of any of these. In preferred embodiments, the annexin A1 derivative includes amino acids that are essential for function of the annexin A1. Amino acids that are essential for function can be identified by methods known in the art, such as site-directed mutagenesis or alanine-scanning mutagenesis (Cunningham et al., Science, 244:1081-1085 (1989)). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al., J. Mol. Biol., 224:899-904 (1992); de Vos et al. Science, 255:306-312 (1992)).

Annexin A1 derivatives include active fragments (peptides which are, for example, 6, 9, 12, 15, 16, 20, 30, 35, 36, 37, 38, 39, 40, 50, 100 or more amino acids in length) that can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites. Fragments can be discrete (not fused to other amino acids or polypeptides) or can be within a larger polypeptide.

Delivery of Agents

In the methods of the invention, an agent is delivered in a neoplasm-specific manner or a neovasculature-specific manner, utilizing an agent that specifically binds to annexin A1 or a derivative of annexin A1, or using annexin A1 or a derivative of annexin A1. An agent that "specifically binds" to annexin A1 (an annexin A1 binding partner) or a derivative of annexin A1, as the term is used herein, is an agent that preferentially or selectively binds to annexin A1 or a derivative of annexin A1. While certain degree of non-specific interaction may occur between the agent that specifically binds and the annexin A1, nevertheless, specific binding, may be distinguished as mediated through specific recognition of annexin A1, in whole or part. Typically specific binding results in a much stronger association between the agent and the annexin A1 than between the agent and other proteins, e.g., other vascular proteins. The affinity constant (Ka, as opposed to Kd) of the agent for its cognate is at least $10^6$ or $10^7$, usually at least $10^8$, alternatively at least $10^9$, alternatively at least $10^{10}$, or alternatively at least $10^{11}$M. It should be noted, also, that "specific" binding may be binding that is sufficiently site-specific to effectively be "specific": for example, when the degree of binding is greater by a higher degree (e.g., equal to or greater than 10-fold, equal to or greater than 20-fold, or even equal to or greater than 100-fold), the binding may become functionally equivalent to binding solely to the targeted protein at a particular location: directed and effective binding occurs with minimal or no delivery to other tissues. Thus, the amount that is functionally equivalent to specific binding can be determined by assessing whether the goal of effective delivery of agents is met with minimal or no binding to other tissues.

In a particular embodiment, the agent is or comprises an antibody that specifically binds annexin A1 or a derivative of annexin A1, or is or comprises a fragment of an antibody (e.g., Fab' fragments). Alternatively, the agent is or comprises another agent that specifically binds to annexin A1 or a derivative of annexin A1 (another "specific binding partner"). Representative specific binding partners include, for example, natural ligands, peptides, small molecules (e.g., inorganic small molecules, organic small molecules, derivatives of small molecules, composite small molecules); aptamers; cells; nanoparticles (e.g., lipid or non-lipid based formulations); lipids; lipoproteins; lipopeptides; lipid derivatives; liposomes; modified endogenous blood proteins used to carry chemotherapeutics.

In yet another embodiment, the agent is or comprises annexin A1 itself, or a derivative of annexin A1. In a further embodiment, the agent specifically binds to a binding partner of annexin A1 or to a binding partner of a derivative of annexin A1. The agent can also comprise a first component that targets annexin A1 or a derivative of annexin A1, or targets a binding partner of annexin A1, as described above, and a second component, that is an active component (e.g., a therapeutic agent or imaging agent, as described in detail below). The agent can be administered by itself, or in a composition (e.g., a pharmaceutical or physiological composition) comprising the agent. It can be administered either in vivo (e.g., to an individual) or in vitro (e.g., to a tissue sample). The methods of the invention can be used not only for human individuals, but also are applicable for veterinary uses (e.g., for other mammals, including domesticated animals (e.g., horses, cattle, sheep, goats, pigs, dogs, cats) and non-domesticated animals.

In the methods of the invention, the agent can be administered by itself, or in a composition (e.g., a physiological or pharmaceutical composition) comprising the agent. For example, the agent can be formulated together with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active agents.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include rechargeable or biodegradable devices, particle acceleration devises ("gene guns") and slow release polymeric devices. If desired, the compositions can be administered into a specific tissue, or into a blood vessel serving a specific tissue (e.g., the carotid artery to target brain). The pharmaceutical compositions can also be administered as part of a combinatorial therapy with other agents, either concurrently or in proximity (e.g., separated by hours, days, weeks, months). The activity of the compositions may be potentiated by other agents administered concurrently or in proximity.

The composition can be formulated in accordance with the routine procedures as a pharmaceutical composition adapted for administration to human beings or animals. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The agent may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Representative methods of delivery of an agent in a neoplasm-specific manner or in an angiogenesis- or neovascular-specific manner are described below in relation to treatment, imaging, and diagnostics.

Therapy

In one embodiment of the invention, methods are available for treating neoplasms or other pathologies in an individual, by administering an annexin A1 therapeutic agent. The term, "treatment" as used herein, can refer to ameliorating symptoms associated with the neoplasm or pathology; to reducing, preventing or delaying metastasis of the neoplasm; to reducing the number, volume, and/or size of one or more neoplasms; and/or to lessening the severity, duration or frequency of symptoms of the neoplasm or pathology. An "annexin A1 therapeutic agent," as used herein, refers to an agent that targets neoplasm(s) or other pathologies for destruction (e.g., a chemotherapeutic agent), or otherwise treats the neoplasm, or reduces or eliminates the effects of neoplasm(s) or pathologies on the individual. Because annexin A1 (or an annexin A1 derivative) appears to be important in neoplasm vascular development, as demonstrated by its appearance in neovasculature, inhibition or removal from the cell surface of annexin A1 and/or annexin A1 derivative will shut down angiogenesis and thereby treat the neoplasm or pathology.

In another embodiment of the invention, methods are available for treating angiogenesis or the development of neovasculature, or other pathologies in an individual, by administering an annexin A1 therapeutic agent. Representative additional conditions which can be treated using the methods described herein include atherosclerosis, diabetes and related sequelae, macular degeneration, heart disease (e.g., from ischemia), emphysema, chronic obstructive pulmonary disease, myocarditis, pulmonary and systemic hypertension and their sequelae, infection, and other conditions relating to expression of inflammatory-, angiogenesis- or neovasculature-related proteins, such as those described herein. Expression of angiogenesis-related proteins is a contributor to a variety of malignant, ischemic, inflammatory, infectious and immune disorders (see, e.g., Carmeleit, P., Nature Medicine 9(6):653-660 (2003); Carmeliet, P. and Jain, R., Nature 407: 249-257 (2000)). Thus, the methods are similarly applicable to such conditions, which are collectively referred to herein as "pathology".

The term, "treatment" as used herein, can refer to ameliorating symptoms associated with the angiogenesis, development of neovasculature, or other pathology; to reducing, preventing or delaying development of angiogenesis or neovasculature; to reducing the number, volume, and/or size of one or more regions of angiogenesis or neovasculature; and/or to lessening the severity, duration or frequency of symptoms of the angiogenesis, neovasculature, or other pathology. Thus, an "annexin A1 therapeutic agent," as used herein, also refers to an agent that targets angiogenesis, development of neovasculature, or other pathologies for destruction (e.g., a chemotherapeutic agent), or otherwise treats angiogenesis or neovasculature, or reduces or eliminates negative effects of angiogenesis, neovasculature, or other pathologies on the individual.

In a further embodiment of the invention, methods are available for enhancing or increasing angiogenesis or development of vasculature in an individual, by administering an annexin A1 neovasculature agent. An "annexin A1 neovasculature agent," as used herein, refers to an agent that enhances or increases angiogenesis or development of neovasculature, or which otherwise treats diseases or conditions which can be ameliorated by enhanced or increased angio genesis or increased development of neovasculature.

In one embodiment, the annexin A1 therapeutic agent or annexin A1 neovasculature agent comprises an agent that specifically binds to annexin A1 or a derivative of annexin A1. In a particular embodiment, the annexin A1 therapeutic agent or annexin A1 neovasculature agent is or comprises an antibody that specifically binds annexin A1 or a derivative of annexin A1, or is or comprises a fragment of an antibody (e.g., Fab' fragments or other antigen binding fragments). An "antibody" is an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes multivalent antibodies as well as antigen binding fragments of antibodies, such as Fab', F(ab')2, Fab, Fv, rIgG, and, inverted IgG, as well as the variable heavy and variable light chain domains. An antibody immunologically reactive with annexin A1 or a derivative of annexin A1 can be generated in vivo or by recombinant methods such as selection of libraries of recombinant antibodies in phage or similar vectors. See, e.g., Huse et al. (1989) Science 246:1275-1281; and Ward, et al. (1989) Nature 341:544-546; and Vaughan et al. (1996) Nature Biotechnology, 14:309-314. An "antigen binding fragment" includes any portion of an antibody that binds to annexin A1 or derivative of annexin A1. An antigen binding fragment may be, for example, a polypeptide including a CDR region, or other fragment of an immunoglobulin molecule which retains the affinity and specificity for annexin A1 or annexin A1 derivative. Representative antibodies include commercially available antibodies (as listed in Linscott's Directory), such as EH17A mAb (SCB); Zym RB pAb (Zymed); 11-29 mAb (ICN biomedicals); 29 mAb (BD Transduction Labs); C19 pAb (SCB); N19 pAb (SCB); and H65 pAb (SCB)).

In another embodiment, other specific binding partners of annexin A1, as described above, can be used as agents that specifically bind to annexin A1 or to a derivative of annexin A1. In yet another embodiment, the annexin A1 therapeutic agent or annexin A1 neovasculature agent is or comprises annexin A1 itself or a derivative of annexin A1. In another embodiment, the annexin A1 therapeutic agent or annexin A1 neovasculature agent is or comprises an agent that specifically binds to a binding partner of annexin A1 or to a binding partner of a derivative of annexin A1. In a further embodiment, the annexin A1 therapeutic agent or annexin A1 neovasculature agent is or comprises a binding partner of annexin A1 or a binding partner of a derivative of annexin A1.

In a further embodiment, the annexin A1 therapeutic agent or annexin A1 neovasculature agent comprises an active agent component and a targeting agent component. The targeting agent component is or comprises an agent that specifically binds to annexin A1 or to a derivative of annexin A1, or specifically binds to a binding partner of annexin A1, as described above. If desired, the targeting agent component can also specifically bind to more than one target (e.g., to annexin A1 and to a derivative of annexin A1; to annexin A1 and to a binding partner of annexin A1, for example). Alternatively, the targeting agent itself is or comprises annexin A1 or a derivative of annexin A1, or a binding partner of annexin A1 or a binding partner of a derivative of annexin A1. Annexin A1 binds to interacting partners that appear on tumor endothelium; when the interaction sites are not saturated, annexin A1 (or a derivative) can home to the site and bind.

In one representative annexin A1 targeting agent, a multivalent antibody is used. One moiety of the multivalent antibody can serve as the targeting agent component, and a second moiety of the multivalent antibody can serve as the active agent component.

The targeting agent component is linked to the active agent component. For example, they can be covalently bonded directly to one another. Where the two are directly bonded to one another by a covalent bond, the bond may be formed by forming a suitable covalent linkage through an active group on each moiety. For instance, an acid group on one compound may be condensed with an amine, an acid or an alcohol on the other to form the corresponding amide, anhydride or ester, respectively.

In addition to carboxylic acid groups, amine groups, and hydroxyl groups, other suitable active groups for forming linkages between a targeting agent component and an active agent component include sulfonyl groups, sulfhydryl groups, and the haloic acid and acid anhydride derivatives of carboxylic acids.

In other embodiments, the targeting agent component and an active agent component may be covalently linked to one another through an intermediate linker. The linker advantageously possesses two active groups, one of which is complementary to an active group on the targeting agent component, and the other of which is complementary to an active group on the active agent component. For example, where the both possess free hydroxyl groups, the linker may suitably be a diacid, which will react with both compounds to form a diether linkage between the two residues. In addition to carboxylic acid groups, amine groups, and hydroxyl groups, other suitable active groups for forming linkages between pharmaceutically active moieties include sulfonyl groups, sulfhydryl groups, and the haloic acid and acid anhydride derivatives of carboxylic acids.

Suitable linkers are set forth in the table below.

| FIRST ACTIVE GROUP | SECOND ACTIVE GROUP | SUITABLE LINKER |
|---|---|---|
| Amine | Amine | Diacid |
| Amine | Hydroxy | Diacid |
| Hydroxy | Amine | Diacid |
| Hydroxy | Hydroxy | Diacid |
| Acid | Acid | Diamine |
| Acid | Hydroxy | Amino acid, hydroxyalkyl acid, sulfhydrylalkyl acid |
| Acid | Amine | Amino acid, hydroxyalkyl acid, sulfhydrylalkyl acid |

Suitable diacid linkers include oxalic, malonic, succinic, glutaric, adipic, pimelic, suberic, azelaic, sebacic, maleic, fumaric, tartaric, phthalic, isophthalic, and terephthalic acids. While diacids are named, the skilled artisan will recognize that in certain circumstances the corresponding acid halides or acid anhydrides (either unilateral or bilateral) are preferred as linker reprodrugs. A preferred anhydride is succinic anhydride. Another preferred anhydride is maleic anhydride. Other anhydrides and/or acid halides may be employed by the skilled artisan to good effect.

Suitable amino acids include -butyric acid, 2-aminoacetic acid, 3-aminopropanoic acid, 4-aminobutanoic acid, 5-aminopentanoic acid, 6-aminohexanoic acid, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Again, the acid group of the suitable amino acids may be converted to the anhydride or acid halide form prior to their use as linker groups.

Suitable diamines include 1,2-diamino ethane, 1,3-diaminopropane, 1,4-diaminobutane, 1,5-diaminopentane, 1,6-diaminohexane. Suitable amino alcohols include 2-hydroxy-1-aminoethane, 3-hydroxy-1-aminoethane, 4-hydroxy-1-aminobutane, 5-hydroxy-1-aminopentane, 6-hydroxy-1-aminohexane.

Suitable hydroxyalkyl acids include 2-hydroxyacetic acid, 3-hydroxypropanoic acid, 4-hydroxybutanoic acid, 5-hydroxypentanoic acid, 5-hydroxyhexanoic acid.

The person having skill in the art will recognize that by selecting the components of the targeting agent component and active agent component having suitable active groups, and by matching them to suitable linkers, a broad palette of inventive compounds may be prepared within the scope of the present invention.

Moreover, the various linker groups can be designated either "weak" or "strong" based on the stability of the covalent bond which the linker functional group will form between the spacer and either the polar lipid carrier or the biologically active compound. The weak functionalities include, but are not limited to phosphoramide, phosphoester, carbonate, amide, carboxyl-phosphoryl anhydride, ester and thioester. The strong functionalities include, but are not limited to ether, thioether, amine, sterically hindered amides and esters. The use of a strong linker functional group between the spacer group and the biologically-active compound will tend to decrease the rate at which the compound will be released at the target site, whereas the use of a weak linker functional group between the spacer group and the compound may act to facilitate release of the compound at the target site.

Enzymatic release is also possible, but such enzyme-mediated modes of release will not necessarily be correlated with bond strength in such embodiments of the invention. Spacer moieties comprising enzyme active site recognition groups, such as spacer groups comprising peptides having proteolytic cleavage sites therein, are envisioned as being within the scope of the present invention. In certain embodiments, the linker moiety includes a spacer molecule which facilitated hydrolytic or enzymatic release of the active agent component from the targeting agent component. In particularly preferred embodiments, the spacer functional group is hydrolyzed by an enzymatic activity found in the target vascular tissue, preferably an esterase.

The active agent component, which is linked to the targeting agent component, can be or comprise any agent that achieves the desired therapeutic result, including agents such as the following, which can be used as an active agent component either for an annexin A1 therapeutic agent or an annexin A1 neovasculature agent, as appropriate: a radionuclide (e.g., I125, 123, 124, 131 or other radioactive agent); a chemotherapeutic agent (e.g., an antibiotic, antiviral or antifungal); an immune stimulatory agent (e.g., a cytokine); an anti-neoplastic agent: an anti-inflammatory agent; a pro-inflammatory agent; a pro-apoptotic agent (e.g., peptides or other agents to attract immune cells and/or stimulate the immune system); a pro-coagulant; a toxin (e.g., ricin, enterotoxin, LPS); an antibiotic; a hormone; a protein (e.g., a recombinant protein or a recombinant modified protein); a carrier protein (e.g., albumin, modified albumin); an enzyme; another protein (e.g., a surfactant protein, a clotting protein); a lytic agent; a small molecule (e.g., inorganic small molecules, organic small molecules, derivatives of small molecules, composite small molecules); aptamers; cells, including modified cells; vaccine-induced or other immune cells; nanoparticles (e.g., lipid or non-lipid based formulations, albumin-based formulations); transferrins; immunoglobulins; multivalent antibodies; lipids; lipoproteins; lipopeptides; liposomes; lipid derivatives; an natural ligand; and altered protein (e.g., albumin or other blood carrier protein-based delivery system, modified to increase affinity for the targeted protein; orosomucoid); an agent that alters the extracellular matrix of the targeted cell; an agents that inhibits growth, migration or formation of vascular structures (for an annexin A1 therapeutic agent); an agent that enhances or increases growth, migration or formation of vascular structures (for an annexin A1 neovasculature agent); a gene or nucleic acid (e.g., an antisense oligonucleotide RNA; siRNA); viral or non-viral gene delivery vectors or systems; or a prodrug or promolecule.

For example, in one embodiment, a radionuclide or other radioactive agent can be used as the active agent component of the annexin A1 therapeutic agent. The targeting agent component delivers the radioactive agent in a neoplasm-specific or neovasculature-specific manner, allowing local radiation damage and resulting in radiation-induced apoptosis and necrosis throughout the neoplasm including in neoplasm cells, stromal calls, and endothelial cells of the tumor, or throughout the area having unwanted neovasculature. Alternatively, in another embodiment, an agent that stimulates or increases angiogenesis or development of neovasculature can be used as an active agent component of the annexin A1 neovasculature agent. The targeting agent component delivers the agent in a specific manner, resulting in increased angiogenesis or increased development of neovasculature at specific sites where annexin A1 is present.

In another particular embodiment, antisense oligonucleotides or other agents can be used as the active agent component, to alter, and particular to inhibit, production of a gene in a targeted tissue, such as a gene that is overexpressed in a neoplasm tissue (e.g., an oncogene or a gene associated with carcinoma, such as c-Jun, c-Fos, HER-2, E2F-1, RAS, FAS, NF, BRCA), or a gene that is overexpressed in angiogenesis. Alternatively, oligonucleotides or genes can be used to alter, and particularly to enhance, production of a protein in the targeted tissue, such as a gene that controls apoptosis or regulates cell growth; oligonucleotides or genes can also be used to produce a protein that is underexpressed or deleted in the targeted tissue, or to express a gene product that is directly or indirectly destructive to the neoplasm.

In a further particular embodiment, an anti-inflammatory agent can be used as the active agent. Representative agents include a non-steroidal anti-inflammatory agent; a steroidal or corticosteroidal anti-inflammatory agent; or other anti-inflammatory agent (e.g., histamine). Alternatively, pro-inflammatory agents can be used as active agents (e.g., to enhance angiogenesis or increase development of neovasculature, as described herein).

In another particular embodiment, chemotherapeutic agents for neoplastic diseases can be used as the active agent component. Representative agents include alkylating agents (nitrogen mustards, ethylenimines, alkyl sulfonates, nitrosoureas, and triazenes), antimetabolites (folic acid analogs such as methotrexate, pyrimidine analogs, and purine analogs), natural products and their derivatives (antibiotics, alkaloids, enzymes), hormones and antagonists (corticosteroids; adrenocorticosteroids, progestins, estrogens), and other similar agents. For example, in certain embodiments, the chemotherapeutic agent can be acytotoxic or cytostatic drugs. Chemotherapeutics may also include those which have other effects on cells such as reversal of the transformed state to a differentiated state or those which inhibit cell replication. Examples of known cytotoxic agents useful in the present invention are listed, for example, in Goodman et al., "The Pharmacological Basis of Therapeutics," Sixth Edition, A. G. Gilman et al, eds./Macmillan Publishing Co. New York, 1980. These include taxol, nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used; such drugs are known to these skilled in the art and include puromycin, cycloheximide, and ribonuclease.

Most of the chemotherapeutic agents currently in use in treating cancer possess functional groups that are amenable to chemical crosslinking directly with an amine or carboxyl group of a targeting agent component. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to a free amino group.

Peptide and polypeptide toxins are also useful as active agent components, and the present invention specifically contemplates embodiments wherein the active agent component is a toxin. Toxins are generally complex toxic products of various organisms including bacteria, plants, etc. Examples of toxins include but are not limited to: ricin, ricin A chain (ricin toxin), Pseudomonas exotoxin (PE), diphtheria toxin (DT), Clostridium perfringens phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

The present invention also contemplates dyes used, for example, in photodynamic therapy, and used in conjunction with appropriate non-ionizing radiation. The use of light and porphyrins in methods of the present invention is also contemplated and their use in cancer therapy has been reviewed. van den Bergh, Chemistry in Britain, 22: 430-437 (1986), which is incorporated herein in its entirety by reference.

In a further particular embodiment, an anti-inflammatory agent can be used as the active agent. Representative agents include a non-steroidal anti-inflammatory agent; a steroidal or corticosteroidal anti-inflammatory agent; or other anti-inflammatory agent (e.g., histamine). Alternatively, pro-inflammatory agents can be used as active agents (e.g., to enhance angiogenesis or increase development of neovasculature, as described herein).

Prodrugs or promolecules can also be used as the active agent. For example, a prodrug that is used as an active agent can subsequently be activated (converted) by administration of an appropriate enzyme, or by endogenous enzyme in the targeted tissue. Alternatively, the activating enzyme can be co-administered or subsequently administered as another active agent as part of a therapeutic agent as described herein; or the prodrug or promolecule can be activated by a change in pH to a physiological pH upon administration. Representative prodrugs include Herpes simplex virus thymidine kinase (HSV TK) with the nucleotide analog GCV; cytosine deaminase ans t-fluorocytosine; alkaline phosphatase/etoposide-phosphate; and other prodrugs (e.g., those described in Greco et al., J. Cell. Phys. 187:22-36, 2001; and Konstantinos et al., Anticancer Research 19:605-614, 1999; see also Connors, T. A., Stem Cells 13(5): 501-511, 1995; Knox, R. J., Baldwin, A. et al., Arch. Biochem. Biophys. 409(1):197-206, 2003; Syrigos, K. N. and Epenetos, A. A., Anticancer Res. 19(1A): 605-613, 1999; Denny, W. A., JBB 1:48-70, 2003).

In another embodiment of the invention, the targeting agent component and/or the active agent component comprises a chelate moiety for chelating a metal, e.g., a chelator for a radiometal or paramagnetic ion. In preferred embodiments, the a chelator is a chelator for a radionuclide. Radionuclides useful within the present invention include gamma-emitters, positron-emitters, Auger electron-emitters, X-ray emitters and fluorescence-emitters, with beta- or alpha-emitters preferred for therapeutic use. Examples of radionuclides useful as toxins in radiation therapy include: 32P, 33P, 43K, 47Sc, 52Fe, 57Co, 64Cu, 67Ga, 67Cu, 68Ga, 71Ge, 75Br, 76Br, 77Br, 77As, 77Br, 81Rb/81MKr, 87MSr, 90Y, 97Ru, 99Tc, 100Pd, 101Rh, 103Pb, 105Rh, 109Pd, 111Ag, 111In, 113In, 119Sb 121Sn, 123I, 125I, 127Cs, 128Ba, 129Cs, 131I, 131Cs, 143Pr, 153Sm, 161Tb, 166Ho, 169Eu, 177Lu, 186Re, 188Re, 189Re, 191Os, 193Pt, 194Ir, 197Hg, 199Au, 203Pb, 211At, 212Pb, 212Bi and 213Bi. Preferred therapeutic radionuclides include 188Re, 186Re, 203Pb, 212Pb, 212Bi, 109Pd, 64Cu, 67Cu, 90Y, 125I, 131I, 77Br, 211At, 97Ru, 105Rh, 198Au and 199Ag, 166Ho or 177Lu. Conditions under which a chelator will coordinate a metal are described, for example, by Gansow et al., U.S. Pat. Nos. 4,831,175, 4,454,106 and 4,472,509.

In one embodiment, for example, 99mTc can be used radioisotope for therapeutic and diagnostic applications (as described below), as it is readily available to all nuclear medicine departments, is inexpensive, gives minimal patient radiation doses, and has ideal nuclear imaging properties. It has a half-life of six hours which means that rapid targeting of a technetium-labeled antibody is desirable. Accordingly, in certain preferred embodiments, the annexin A1 therapeutic agent includes a chelating agents for technium.

The annexin A1 therapeutic agent can also comprise radiosensitizing agents, e.g., a moiety that increase the sensitivity of cells to radiation. Examples of radiosensitizing agents include nitroimidazoles, metronidazole and misonidazole (see: DeVita, V. T. Jr. in Harrison's Principles of Internal Medicine, p. 68, McGraw-Hill Book Co., N.Y. 1983, which is incorporated herein by reference). The annexin A1 therapeutic agent that comprises a radiosensitizing agent as the active moiety is administered and localizes in the endothelial call and/or in any other cells of the neoplasm. Upon exposure of the individual to radiation, the radiosensitizing agent is "excited" and causes the death of the cell.

There are a wide range of moieties which can serve as chelating ligands and which can be derivatized as part of the annexin A1 therapeutic agent. For instance, the chelating ligand can be a derivative of 1,4,7,10-tetraazacyclododecane-tetraacetic acid (DOTA), ethylenediaminetetraacetic acid (EDTA), diethylenetriaminepentaacetic acid (DTPA) and 1-p-Isothiocyanato-benzyl-methyl-diethylenetriaminepen-taacetic acid (ITC-MX). These chelators typically have groups on the side chain by which the chelator can be used for attachment to a targeting agent component. Such groups include, e.g., benzylisothiocyanate, by which the DOTA, DTPA or EDTA can be coupled to, e.g., an amine group of the inhibitor.

In one embodiment, the agent is an "NxSy" chelate moiety. As defined herein, the term "NxSy chelates" includes bifunctional chelators that are capable of coordinately binding a metal or radiometal and, preferably, have N2S2 or N3S cores. Exemplary NxSy chelates are described, e.g., in Fritzberg et al. (1988) PNAS 85:4024-29; and Weber et al. (1990) Bioconjugate Chem. 1:431-37; and in the references cited therein. The Jacobsen et al. PCT application WO 98/12156 provides methods and compositions, i.e. synthetic libraries of binding moieties, for identifying compounds which bind to a metal atom. The approach described in that publication can be used to identify binding moieties which can subsequently be incorporated into annexin A1 therapeutic agents.

A problem frequently encountered with the use of conjugated proteins in radiotherapeutic and radiodiagnostic applications is a potentially dangerous accumulation of the radio labeled moiety fragments in the kidney. When the conjugate is formed using a acid-or base-labile linker, cleavage of the radioactive chelate from the protein can advantageously occur. If the chelate is of relatively low molecular weight, it is not retained in the kidney and is excreted in the urine, thereby reducing the exposure of the kidney to radioactivity. However, in certain instances, it may be advantageous to utilize acid-or base-labile linkers in the subject ligands for the same reasons they have been used in labeled proteins.

Other appropriate active agents include agents that induce intravascular coagulation, or which damage the endothelium, thereby causing coagulation and effectively infracting a neoplasm or other targeted pathology. In addition, if desired, enzymes activated by other agents (e.g., biotin, activated by avidin) can be used as active agents or as part of the therapeutic targeting agent.

The annexin A1 therapeutic agents can be synthesized, by standard methods known in the art (e.g., by recombinant DNA technology or other means), to provide reactive functional groups which can form acid-labile linkages with, e.g., a carbonyl group of the ligand. Examples of suitable acid-labile linkages include hydrazone and thiosemicarbazone functions. These are formed by reacting the oxidized carbohydrate with chelates bearing hydrazide, thiosemicarbazide, and thiocarbazide functions, respectively. Alternatively, base-cleavable linkers, which have been used for the enhanced clearance of the radiolabel from the kidneys, can be used. See, for example, Weber et al. 1990 Bioconjug. Chem. 1:431. The coupling of a bifunctional chelate via a hydrazide linkage can incorporate base-sensitive ester moieties in a linker spacer arm. Such an ester-containing linker unit is exemplified by ethylene glycolbis(succinimidyl succinate), (EGS, available from Pierce Chemical Co., Rockford, Ill.), which has two terminal N-hydroxysuccinimide (NHS) ester derivatives of two 1,4-dibutyric acid units, each of which are linked to a single ethylene glycol moiety by two alkyl esters. One NHS ester may be replaced with a suitable amine-containing BFC (for example 2-aminobenzyl DTPA), while the other NHS ester is reacted with a limiting amount of hydrazine. The resulting hyrazide is used for coupling to the targeting agent component, forming an ligand-BFC linkage containing two alkyl ester functions. Such a conjugate is stable at physiological pH, but readily cleaved at basic pH.

Annexin A1 therapeutic agents labeled by chelation are subject to radiation-induced scission of the chelator and to loss of radioisotope by dissociation of the coordination complex. In some instances, metal dissociated from the complex can be re-complexed, providing more rapid clearance of non-specifically localized isotope and therefore less toxicity to non-target tissues. For example, chelator compounds such as EDTA or DTPA can be infused into patients to provide a pool of chelator to bind released radiometal and facilitate excretion of free radioisotope in the urine.

In still other embodiments, a Boron addend, such as a carborane, can be used. For example, carboranes can be prepared with carboxyl functions on pendant side chains, as is well known in the art. Attachment of such carboranes to an amine functionality, e.g., as may be provided on the targeting agent component can be achieved by activation of the carboxyl groups of the carboranes and condensation with the amine group to produce the conjugate. Such therapeutic agents can be used for neutron capture therapy.

In a further embodiment, RNAi is used. "RNAi construct" is a generic term used throughout the specification to include small interfering RNAs (siRNAs), hairpin RNAs, and other RNA species which can be delivered ectopically to a cell, cleaved by the enzyme dicer and cause gene silencing in the cell. The term "small interfering RNAs" or "RNAs" refers to nucleic acids around 19-30 nucleotides in length, and more preferably 21-23 nucleotides in length. The RNAs are double-stranded, and may include short overhangs at each end. Preferably, the overhangs are 1-6 nucleotides in length at the 3' end. It is known in the art that the RNAs can be chemically synthesized, or derive by enzymatic digestion from a longer double-stranded RNA or hairpin RNA molecule. For efficiency, an RNA will generally have significant sequence similarity to a target gene sequence. Optionally, the RNA molecules includes a 3' hydroxyl group, though that group may be modified with a fatty acid moiety as described herein. The phrase "mediates RNAi" refers to (indicates) the ability of an RNA molecule capable of directing sequence-specific gene silencing, e.g., rather than a consequence of induction of a sequence-independent double stranded RNA response, e.g., a PKR response.

In certain embodiments, the RNAi construct used for the active agent component is a small-interfering RNA (RNA), preferably being 19-30 base pairs in length. Alternatively, the RNAi construct is a hairpin RNA which can be processed by cells (e.g., is a dicer substrate) to produce metabolic products in common with RNA treated cells, e.g., a processed to short (19-22 mer) guide sequences that induce sequence specific gene silencing. In a preferred embodiment, the treated animal is a human.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the RNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro.

The RNAi constructs may include other modifications, such as to the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general cellular response to dsRNA (a "PKR-mediated response"). Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying other RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioate, phosphorodithioate, methylphosphonate, chimeric methylphosphonate-phosphodiesters, phosphoramidate, boranophosphate, phosphotriester, formacetal, 3'-thio formacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene(methylimino) (MMI), methyleneoxy(methylimino) (MOMI) linkages, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell.

In certain embodiments, to reduce unwanted immune stimulation, the RNAi construct is designed so as not to include unmodified cytosines occurring 5' to guanines, e.g., to avoid stimulation of B cell mediated immunosurveillance.

In certain embodiments in which the RNAi is to be delivered for local therapeutic effect, the backbone linkages can be chosen so as titrate the nuclease sensitivity to make the RNAi sufficiently nuclease resistant to be effective in the tissue of interest (e.g., the neoplasm), but not so nuclease resistant that significant amounts of the construct could escape the tissue undegraded. With the use of this strategy, RNAi constructs are available for gene silencing in the tissue of interest, but are degraded before they can enter the wider circulation.

The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications Inhibition is sequence-specific in that nucleotide sequences corresponding to the duplex region of the RNA are targeted for genetic inhibition.

In certain embodiments, the subject RNAi constructs are siRNAs. These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Modification of siRNA molecules with fatty acids can be carried out at the level of the precursors, or, perhaps more practically, after the RNA has been synthesized. The latter may be accomplished in certain instances using nucleoside precursors in the synthesis of the polymer that include functional groups for formation of the linker-fatty acid moiety.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci U S A, 2002, 99:6047-

52). Preferably, such hairpin RNAs are engineered in cells or in an animal to ensure continuous and stable suppression of a desired gene. It is known in the art that siRNAs can be produced by processing a hairpin RNA in the cell.

The annexin A1 therapeutic agent, alone or in a composition, is administered in a therapeutically effective amount, which is the amount used to treat the neoplasm or to treat angiogenesis or unwanted development of neovasculature. The amount which will be therapeutically effective will depend on the nature of the neoplasm, neovasculature or angiogenesis, the extent of disease and/or metastasis, and other factors, and can be determined by standard clinical techniques. In addition, in vitro or in vivo assays may optionally be employed to help identify optimal dosage ranges. The precise dose to be employed in the formulation will also depend on the route of administration, and the seriousness of the symptoms, and should be decided according to the judgment of a practitioner and each patient's circumstances. Effective doses may be extrapolated from dose-response curves derived from in vitro or animal model test systems.

Although the embodiments above describe treatment of undesirable angiogenesis, development of neovasculature, or other pathologies, the methods are also applicable to situations in which angiogenesis or development of neovasculature is desirable (e.g., regrowth of blood vessels after reattachment of a previously severed body part; development of blood vessels to compensate for damaged blood vessels after myocardial infarction; or for other injury or disease which is treated by improving blood flow, tissue repair, development of neovasculature and angiogenesis). In this embodiment, an annexin A1 neovasculature agent comprises a compound (e.g., as the active agent component) that enhances angiogenesis or development of neovasculature. The term, "treatment" as used in this specific embodiment, refers to enhancing or increasing angiogenesis or neovasculature. The agent can administered by the methods described above, using pharmaceutical compositions such as those described above.

In addition, in a further embodiment of the invention, annexin A1 as described herein can be used as focal point for immune stimulation, in order to effect immune attack by a patient's own immune system annexin A1 annexin A1. In one embodiment, cells can be modified to produce annexin A1 : for example, dendritic cells from an individual can be isolated, and then inoculated with annexin A1 or an antigenic fragment of the targeted protein, and then the dendritic cells can be readministered to the individual to initiate an immune attack against annexin A1. In addition, T cells specific for annexin A1 or fragments thereof, including cells induced by vaccination, can be isolated and used directly to attack the neoplasm immunologically. Alternatively, an annexin A1 therapeutic agent comprising a targeted protein expressed on endothelial cell surface can be administered to generate immune response. Other standard techniques for stimulating immune system attack can be used as well. In this manner, 'personalized medicine' for each patient can be designed, to target the particular individual's neoplasm or other pathology. Thus, a method of treating neoplasia in an individual by administering to the individual an annexin A1 therapeutic agent that comprises annexin A1, and generating an immune response against the targeted protein, is now available.

Imaging In Vivo and Diagnostics

The present invention also relates to methods of delivering imaging agents in a neoplasm-specific manner, for physical imaging, e.g., for use in assessing an individual for the presence of a neoplasm, including primary and/or secondary (metastatic) neoplasms, as well as to the use of the described agents for manufacture of medicaments for use in physical imaging. In the methods of the invention, the imaging agent is delivered to, into and/or across vascular endothelium in a neoplasm-specific manner through an agent of interest. "Neoplasm-specific" indicates that the agent preferentially or selectively binds to a neoplasm. The present invention also relates to methods of delivering imaging agents in a neovasculature-specific manner, for physical imaging, e.g., for use in assessing an individual for the presence of angiogenesis or of neovasculature. In the methods of the invention, the imaging agent is delivered to, into and/or across vascular endothelium in a neovasculature-specific manner through an agent of interest. "Neovasculature-specific" indicates that the agent preferentially or selectively binds to new blood vessel growth. It is noted that new blood vessels, "neovasculature," may be in varying stages of development and at different stages of maturity; for the purposes of this application, "neovasculature" refers to new blood vessel growth that differs from normal vasculature, either in stage, maturity, or other relevant characteristic.

The agent of interest comprises a targeting agent component and an imaging agent component. In one embodiment, the targeting agent component can be an agent that specifically binds to annexin A1 or a derivative of annexin A1, as described above. In a particular embodiment, the targeting agent component can be an antibody that specifically binds annexin A1 or a derivative of annexin A1, or is a fragment of an antibody (e.g., Fab' fragments). The antibody can be a humanized antibody, if desired. Representative antibodies include those described above. In another embodiment, other specific binding partners of annexin A1 can be used as targeting agent components, including agents that specifically bind to annexin A1 or to a derivative of annexin A1 (e.g., natural ligands, peptides). In yet another embodiment, the targeting agent component is annexin A1 itself, or a derivative of annexin A1; alternatively, the targeting agent component can be an agent that specifically binds to a binding partner of annexin A1 or to a binding partner of a derivative of annexin A1.

The imaging agent component (comprising the imaging agent, and, if necessary, other components such as a means to couple the imaging agent component to the targeting agent component) can be, for example, a radioactive agent (e.g., radioiodine (125I, 131I); technetium; yttrium; 35S or 3H) or other radioisotope or radiopharmaceutical; a contrast agent (e.g., gadolinium; manganese; barium sulfate; an iodinated or noniodinated agent; an ionic agent or nonionic agent); a magnetic agent or a paramagnetic agent (e.g., gadolinium, ironoxide chelate); liposomes (e.g., carrying radioactive agents, contrast agents, or other imaging agents); ultrasound agents (e.g., microbubble-releasing agents); nanoparticles; a gene vector or virus inducing a detecting agent (e.g., including luciferase or other fluorescent polypeptide); an enzyme (horseradish peroxidase, alkaline phosphatase, β-galactosidase, or acetylcholinesterase); a prosthetic group (e.g., streptavidin/biotin and avidin/biotin); a fluorescent material (e.g., umbelliferone, fluorescein, fluorescein isothiocyanate, rhodamine, dichlorotriazinylamine fluorescein, dansyl chloride or phycoerythrin); a luminescent material (e.g., luminol); a bioluminescent material (e.g., luciferase, luciferin, aequorin); or any other imaging agent that can be employed for imaging studies (e.g., for CT, fluoroscopy, SPECT imaging, optical imaging, PET, MRI, gamma imaging).

The imaging agent can be used in methods of performing physical imaging of an individual. "Physical imaging," as used herein, refers to imaging of all or a part of an individual's body (e.g., by the imaging studies methods set forth above).

These methods of physical imaging can be used, for example, to assess an individual for the presence or absence, or extent, of a neoplasm (e.g., by "positive" imaging), including primary and/or metastatic neoplasms, or to assess an individual for the presence or absence, or extent, or angiogenesis or of neovasculature. In a preferred embodiment, the physical imaging can be "positive," that is, can be used to detect the presence of a neoplasm, angiogenesis, or neovasculature. Physical imaging permits visualization and/or detection of abnormal pathology or angiogenesis or neovasculature, and can be used to quantify or determine the extent, size, location and/or number of a type of neoplasm or of new blood vessel growth. Thus, an estimate can be made of the extent of disease, facilitating, for example, clinical diagnosis and/or prognosis.

For physical imaging, an imaging agent is administered to the individual, either by itself or in a physiologically acceptable carrier, by a means that allows the imaging agent to contact an endothelial cell surface (e.g., intravenously); upon administration, the targeted imaging agents can be visualized noninvasively by conventional external detection means (designed for the imaging agent), to detect the preferential or specific accumulation of the agent of interest in the neoplasm. A "concentration," as used herein, is an amount of the agent of interest at a particular location in the individual's body that is greater than would be expected from mere circulation or diffusion of the agent of interest in the individual. A concentration is indicative of binding of the agent of interest to the neoplasm or to new blood vessels, and thus is indicative of the presence of the neoplasm or of angiogenesis or neovasculature. These methods can be used to assess an individual for the presence or absence not only of primary neoplasms, but also of metastases, as well as for angiogenesis or neovasculature. Representative new blood vessel growth includes, for example, growth related to a variety of diseases, including, for example, atherosclerosis, macular degeneration or diabetic retinopathy, or acute or chronic inflammation. In another embodiment of imaging in vivo, an imaging agent as described herein can be used to facilitate imaging-assisted therapy, such as surgical removal of a neoplasm or surgical removal of undesirable new blood vessel growth.

In another embodiment of imaging in vivo, an imaging agent as described herein can be used to facilitate surgical removal of a neoplasm or to facilitate surgical removal of undesirable new blood vessel growth. For example, an imaging agent, such as an imaging agent that comprises a luminescent component, is administered to an individual in a manner such that the imaging agent targets neoplasm(s) or new blood vessel growth in the individual. A surgeon can then identify the presence of the imaging agent (through luminescence, for example), and is more easily able to remove neoplastic tissue or new blood vessel growth (angiogenic tissue) that has thus been tagged with the imaging agent.

Furthermore, the growth, regression, or metastasis of a neoplasm, as well as the growth or regression of new blood vessels, can be assessed by serial imaging of an individual in this manner; each imaging session provides a view of the extent, size, location and/or number of neoplasm(s) or of new blood vessels.

If desired, the imaging agent can further comprise a therapeutic agent. A "therapeutic agent," as used herein, refers to an agent that targets neoplasm(s), new blood vessels (angiogenic tissue) or other pathologies for destruction (e.g., a chemotherapeutic agent) or otherwise reduces or eliminates the effects of neoplasm(s), angiogenic tissue, or pathologies on the individual. Additional uses of therapeutic agents are discussed above in relation to therapy.

Although the embodiments above describe imaging of undesirable angiogenesis or neovasculature, the methods are equally applicable to situations in which angiogenesis or development of neovasculature is desirable (e.g., as described above in relation to treatment). In these methods, angiogenesis or neovasculature is similarly assessed by administration of an imaging agent as described above. If desired, the imaging agent can further comprise a therapeutic agent such as an annexin A1 neovasculature agent, which enhances/increases angiogenesis or development of neovasculature, as discussed above in relation to therapy.

Imaging Ex Vivo and Diagnostics

In another embodiment, the present invention relates to methods of delivering imaging agents in a neoplasm-specific manner or a neovasculature-specific manner, e.g., for use ex vivo for analysis of a tissue sample or cell sample. The term, "tissue sample," as used herein, refers not only to a sample from tissue (e.g., skin, brain, breast, lung, kidney, prostate, ovarian, head and neck, liver, or other organ), but also to a blood sample. The tissue can be normal tissue, benign or malignant, or a combination thereof (e.g., a biopsy sample), and can also comprise a tissue for which the status (normal, benign or malignant) is unknown.

In one embodiment of the invention, an imaging agent, as described above, is used to perform ex vivo imaging. "Ex vivo imaging," as used herein, refers to imaging of a tissue sample or cell sample that has been removed from an individual's body (e.g., by surgical removal of a tissue sample such as a neoplasm sample, or a cell sample; by venipuncture; or other means). The imaging permits visualization and/or detection of abnormal pathology (e.g., neoplasm or angiogenic tissue (new blood vessel growth)), and can be used to quantify or determine the extent, size, location and/or number of a type of neoplasm(s) or of new blood vessel growth in a sample. Thus, an estimate can be made of the extent of disease, facilitating, for example, clinical diagnosis and/or prognosis.

In one embodiment, for ex vivo imaging, the imaging agent is administered to an individual as described above. A biopsy sample can then be taken from the individual, and the biopsy sample can then be assessed for the presence or absence of a concentration of the agent of interest. Alternatively, in another embodiment of ex vivo imaging, the imaging agent is applied to a tissue sample. The tissue sample can then be assessed for the presence or absence of a concentration of the agent of interest. A "concentration," as used herein, is an amount of the agent of interest that is greater than would be expected from mere diffusion of the agent of interest in the sample. A concentration is indicative of binding of the agent of interest, and thus is indicative of the presence of neoplasm or neoplasm or new blood vessel growth (angiogenesis or neovasculature). These methods can be used to assess a biopsy or tissue sample to determine whether a neoplasm is malignant (i.e., demonstrates a concentration of the agent of interest, corresponding to a concentration of annexin A1) or benign, or whether there is a presence of new blood vessel growth. In a preferred embodiment, the tissue sample used for ex vivo imaging is a biopsy sample. A concentration, as used herein in relationship to ex vivo imaging, is an amount of the agent of interest at a particular location in the sample that is greater than would be expected from mere circulation or diffusion of the agent of interest into or in the sample. A concentration is indicative of binding of the agent of interest to the neoplasm, and thus is indicative of the presence of the neoplasm. These methods can be used to assess an individual for the presence or absence not only of primary neoplasms, but also of metastases, or of new blood vessel growth (angiogenesis or neovasculature).

Although the embodiments above describe imaging of undesirable angiogenesis or neovasculature ex vivo, the methods are equally applicable to situations in which angiogenesis or neovasculature is desirable, as described above in relation to treatment and in vivo imaging.

Assessment of Treatment Efficacy and Prognosis

Because annexin A1 is usually a cytosolic protein that is able to exist easily in aqueous solutions, its presence in the blood is in equilibrium with its binding at the endothelial cell surface. This indicates that the presence of annexin A1 or its derivatives at the endothelial cell surface allows specific interaction with lipids and/or proteins, such that an assessment of the level of annexin A1 in a blood or serum sample from the individual both before, and during or after, treatment with an annexin A1 therapeutic agent or other therapeutic agent may indicate whether the treatment has successfully decreased a neoplasm, angiogenesis or neovasculature, as indicated by a reduced amount of annexin A1. Alternatively, the in vitro and/or ex vivo diagnosis methods described above can be used in methods for assessment of treatment efficacy in a patient. Thus, the current invention also pertains to methods of monitoring the response of an individual to treatment with a therapeutic agent, such as a therapeutic targeting agent, as described above, or other therapeutic agent, as well as to determine the efficacy of treatment, by comparing the quantity, extent, size, and/or number of neoplasms or of new blood vessel growth (angiogenesis or neovasculature) both before and during or after treatment.

For example, in one aspect of the invention, an individual can be assessed for response to treatment with an annexin A1 therapeutic agent or other therapeutic agent, by examining the individual's annexin A1 level in different tissues, cells and/or body fluids. Blood, serum, plasma or urinary levels of annexin A1, or ex vivo production of annexin A1, can be measured before, and during or after treatment with the annexin A1 therapeutic agent or other therapeutic agent, as can levels of annexin A1 in tissues. The level before treatment is compared with the level during or after treatment. The efficacy of treatment is indicated by a decrease in annexin A1 availability or production: a level of annexin A1 during or after treatment that is significantly lower than the level before treatment, is indicative of efficacy. A level that is lower during or after treatment can be shown, for example, by decreased serum or urinary levels of annexin A1, or decreased ex vivo production of annexin A1. A level that is "significantly lower", as used herein, is a level that is less than the amount that is typically found in control individual(s) or control sample(s), or is less in a comparison of disease in a population associated with the other bands of measurement (e.g., the mean or median, the highest quartile or the highest quintile) compared to lower bands of measurement (e.g., the mean or median, the other quartiles; the other quintiles).

For example, the level of annexin A1 (e.g., in a blood or serum sample, or in a tissue sample) is assessed in a sample from an individual before treatment with an annexin A1 therapeutic agent or other therapeutic agent; and during or after treatment with the annexin A1 therapeutic agent or other therapeutic agent, and the levels are compared. A level of annexin A1 during or after treatment that is significantly lower than the level of annexin A1 before treatment, is indicative of efficacy of treatment with the annexin A1 therapeutic agent or other therapeutic agent. In another aspect, production of annexin A1 is analyzed in a first test sample from the individual, and is also determined in a second test sample from the individual, during or after treatment, and the level of production in the first test sample is compared with the level of production in the second test sample. A level in the second test sample that is significantly lower than the level in the first test sample is indicative of efficacy of treatment.

In another embodiment, in vivo methods as described above can be used to compare images before and after treatment with an annexin A1 therapeutic agent or other therapeutic agent. The extent, size, location and/or number of neoplasms or of angiogenesis or neovasculature in vivo before treatment is compared with the extent, size, location and/or number during or after treatment. The efficacy of treatment is indicated by a decrease of the extent, size, location and/or number of neoplasms, or a decrease in the extent of new blood vessel growth (angiogenesis or neovasculature) as indicated by decreased concentrations of imaging agents. Alternatively, the ex vivo methods as described above can be used to compare biopsy samples before and after treatment with an annexin A1 therapeutic agent or other therapeutic agent. The extent, size, location and/or number of neoplasms or angiogenesis or neovasculature in a sample before treatment is compared with the extent, size, location and/or number in a sample during or after treatment. The efficacy of treatment is indicated by a decrease the extent, size, location and/or number of neoplasms, or the size, location(s) of new blood vessel growth (angiogenesis or neovasculature), as indicated by decreased concentrations of imaging agents. In another embodiment, in vivo methods as described above can be used to image before, during and after treatment with an annexin A1 therapeutic agent or other therapeutic agent. For example, the extent, size, location and/or number of neoplasms, angiogenesis or neovasculature can be assessed by in vivo imaging, and a therapeutic agent (such as an annexin A1 therapeutic agent or other therapeutic agent) is then administered to the individual. Continued, continuous or subsequent imaging of the individual can reveal real-time targeting and destruction of neoplasm cells or of new blood vessel growth.

In another embodiment of the invention, the level of annexin A1 can be used to assess a sample for the presence of aggressive disease and/or to assess prognosis for the patient from whom the tissue sample was obtained. Because the presence of annexin A1 in tumor endothelium is indicative of angiogenesis, the amount of annexin A1 is indicative of the degree of aggression of disease: higher amounts of annexin A1 are indicative of higher angiogenesis, which similarly corresponds to a poorer prognosis. Aggressive disease will show an increased amount of annexin A1 in tumors, compared to less aggressive disease. For example, in one aspect of the invention, an individual can be assessed to determine annexin A1 level in different tissues, cells and/or body fluids. Blood, serum, plasma or urinary levels of annexin A1, or ex vivo production of annexin A1, can be assessed. A level of annexin A1 that is significantly higher is indicative or aggressive disease and/or poorer prognosis. A level that is "significantly higher," as used herein, is a level that is greater than the amount that is typically found in a control individual(s) or control sample(s), or is greater in a comparison of disease in a population associated with the other bands of measurement (e.g., the mean or median, the highest quartile or the highest quintile) compared to lower bands of measurement (e.g., the mean or median, the other quartiles; the other quintiles). Alternatively, an individual can be assessed to determine the annexin A1 level in vivo through in vivo imaging as described above.

These embodiments above can similarly be used for assessment of treatment to enhance angiogenesis or development of neovasculature. The methods are performed as described, except that in these embodiments, efficacy is indicated by increased level of angiogenesis or development of neovasculature as indicated by increased concentrations of imaging agents.

Screening Assays for Agents Altering Annexin Activity

In another embodiment, the invention provides methods for identifying agents (e.g., fusion proteins, polypeptides, peptidomimetics, prodrugs, receptors, binding agents, antibodies, small molecules or other drugs, or ribozymes) which alter (e.g., increase or decrease) the activity of annexin A1 or an annexin A1 derivative as described herein, or which otherwise interact with annexin A1 or an annexin A1 derivative. For example, such agents can be agents which bind to annexin A1 or an annexin A1 derivative; which have a stimulatory or inhibitory effect on, for example, activity of annexin A1 or an annexin A1 derivative; which change (e.g., enhance or inhibit) the ability of annexin A1 or an annexin A1 derivative to interact with binding partners (e.g., receptors or other binding agents); or which alter posttranslational processing of annexin A1 or an annexin A1 derivative (e.g., agents that alter proteolytic processing to direct the polypeptide from where it is normally synthesized to another location in the cell, such as the cell surface; agents that alter proteolytic processing such that more active polypeptide is released from the cell, etc.).

In one embodiment, the invention provides assays for screening candidate or test agents that bind to or modulate the activity of annexin A1 or an annexin A1 derivative, as well as agents identifiable by the assays. Test agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) Anticancer Drug Des., 12:145).

In one embodiment, to identify agents which alter the activity (including the function) of annexin A1 or an annexin A1 derivative, a cell, cell lysate, or solution containing or expressing annexin A1 or an annexin A1 derivative, can be contacted with an agent to be tested; alternatively, the polypeptide can be contacted directly with the agent to be tested. The level (amount) of activity of annexin A1 or the annexin A1 derivative is assessed (e.g., the level (amount) of activity is measured, either directly or indirectly), and is compared with the level of activity in a control (i.e., the level of activity of annexin A1 or the annexin A1 derivative in the absence of the agent to be tested). If the level of the activity in the presence of the agent differs, by an amount that is statistically significant, from the level of the activity in the absence of the agent, then the agent is an agent that alters the activity of annexin A1 or the annexin A1 derivative. An increase in the level of activity relative to a control, indicates that the agent is an agent that enhances (is an agonist of) activity. Similarly, a decrease in the level of activity relative to a control, indicates that the agent is an agent that inhibits (is an antagonist of) activity. In another embodiment, the level of activity of annexin A1 or the annexin A1 derivative in the presence of the agent to be tested, is compared with a control level that has previously been established. A level of the activity in the presence of the agent that differs from the control level by an amount that is statistically significant indicates that the agent alters activity.

The present invention also relates to an assay for identifying agents which alter the expression of annexin A1 or an annexin A1 derivative (e.g., antisense nucleic acids, fusion proteins, polypeptides, peptidomimetics, prodrugs, receptors, binding agents, binding partners, antibodies, small molecules or other drugs, or ribozymes) which alter (e.g., increase or decrease) expression (e.g., transcription or translation) of the gene or nucleic acid encoding annexin A1 or the annexin A1 derivative, as well as agents identifiable by the assays. For example, a solution containing a nucleic acid encoding annexin A1 or an annexin A1 derivative can be contacted with an agent to be tested. The solution can comprise, for example, cells containing the nucleic acid or cell lysate containing the nucleic acid; alternatively, the solution can be another solution which comprises elements necessary for transcription/translation of the nucleic acid. Cells not suspended in solution can also be employed, if desired. The level and/or pattern of annexin A1 or annexin A1 derivative expression (e.g., the level and/or pattern of mRNA or of protein expressed, such as the level and/or pattern of different splicing variants) is assessed, and is compared with the level and/or pattern of expression in a control (i.e., the level and/or pattern of the expression in the absence of the agent to be tested). If the level and/or pattern in the presence of the agent differs, by an amount or in a manner that is statistically significant, from the level and/or pattern in the absence of the agent, then the agent is an agent that alters the expression of annexin A1 or the annexin A1 derivative. Enhancement of expression indicates that the agent is an agonist of activity. Similarly, inhibition of expression indicates that the agent is an antagonist of activity.

In another embodiment of the invention, agents which alter the expression of a gene or nucleic acid encoding annexin A1 or an annexin A1 derivative, can be identified using a cell, cell lysate, or solution containing a nucleic acid encoding the promoter region of the annexin A1 gene operably linked to a reporter gene. After contact with an agent to be tested, the level of expression of the reporter gene (e.g., the level of mRNA or of protein expressed) is assessed, and is compared with the level of expression in a control (i.e., the level of the expression of the reporter gene in the absence of the agent to be tested). If the level in the presence of the agent differs, by an amount or in a manner that is statistically significant, from the level in the absence of the agent, then the agent is an agent that alters the expression of annexin A1, as indicated by its ability to alter expression of a gene that is operably linked to the annexin A1 promoter. Enhancement of the expression of the reporter indicates that the agent is an agonist of activity. Similarly, inhibition of the expression of the reporter indicates that the agent is an antagonist of activity. In another embodiment, the level of expression of the reporter in the presence of the agent to be tested, is compared with a control level that has previously been established. A level in the presence of the agent that differs from the control level by an amount or in a manner that is statistically significant indicates that the agent alters annexin A1 expression.

In other embodiments of the invention, assays can be used to assess the impact of a test agent on the activity of annexin A1 or an annexin A1 derivative in relation to an annexin A1 binding partner, as described above. For example, a cell that expresses a compound that interacts with annexin A1 or an annexin A1 derivative is contacted with annexin A1 or an annexin A1 derivative in the presence of a test agent, and the ability of the test agent to alter the interaction between annexin A1 or the annexin A1 derivative and the annexin A1 binding partner is determined. Alternatively, a cell lysate or a solution containing the annexin A1 binding partner, can be used. An agent which binds to annexin A1 or an annexin A1 derivative, or to the annexin A1 binding partner, can alter the interaction by interfering with, or enhancing the ability of annexin A1 or the annexin A1 derivative to bind to, associate with, or otherwise interact with the annexin A1 binding partner. Determining the ability of the test agent to bind to annexin A1 or an annexin A1 derivative, or to an annexin A1 binding partner can be accomplished, for example, by coupling the test agent with a radioisotope or enzymatic label such that binding of the test agent to the polypeptide can be determined by detecting the labeled with 125I, 35S, 14C, or 3H, either directly or indirectly, and the radioisotope detected by direct counting of radioemmission or by scintillation counting. Alternatively, test agents can be enzymatically labeled with, for example, horseradish peroxidase, alkaline phosphatase, or luciferase, and the enzymatic label detected by determination of conversion of an appropriate substrate to product. It is also within the scope of this invention to determine the ability of a test agent to interact with annexin A1 or an annexin A1 derivative without the labeling of any of the interactants. For example, a microphysiometer can be used to detect the interaction of a test agent with annexin A1 or an annexin A1 derivative, or an annexin A1 binding partner, without the labeling of either the test agent, annexin A1 or annexin A1 derivative, or the annexin A1 binding partner. McConnell, H. M. et al. (1992) Science, 257:1906-1912. As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and polypeptide.

In another embodiment of the invention, assays can be used to identify polypeptides that interact with annexin A1 or an annexin A1 derivative. For example, a yeast two-hybrid system such as that described by Fields and Song (Fields, S. and Song, O., Nature 340:245-246 (1989)) can be used to identify polypeptides that interact with annexin A1 or an annexin A1 derivative. In such a yeast two-hybrid system, vectors are constructed based on the flexibility of a transcription factor which has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used which includes a nucleic acid encoding a DNA binding domain and also annexin A1 or an annexin A1 derivative, and a second vector is used which includes a nucleic acid encoding a transcription activation domain and also a nucleic acid encoding a polypeptide which potentially may interact with annexin A1 or an annexin A1 derivative (e.g., an annexin A1 binding partner or receptor). Incubation of yeast containing the first vector and the second vector under appropriate conditions (e.g., mating conditions such as used in the Matchmaker™ system from Clontech) allows identification of colonies which express the markers of interest. These colonies can be examined to identify the polypeptide(s) which interact with the annexin A1 or annexin A1 derivative. Such polypeptides may be useful as agents which alter the activity of expression of annexin A1 or an annexin A1 derivative.

In more than one embodiment of the above assay methods, it may be desirable to immobilize either the annexin A1 or the annexin A1 derivative, or the annexin A1 binding partner, or other components of the assay on a solid support, in order to facilitate separation of complexed from uncomplexed forms of the polypeptides, as well as to accommodate automation of the assay. Binding of a test agent to the annexin A1 or the annexin A1 derivative or interaction of the annexin A1 or the annexin A1 derivative with a binding partner in the presence and absence of a test agent, can be accomplished in any vessel suitable for containing the reactants. Examples of such vessels include microtitre plates, test tubes, and micro-centrifuge tubes. In one embodiment, a fusion protein (e.g., a glutathione-S-transferase fusion protein) can be provided which adds a domain that allows annexin A1 or annexin A1 derivative or an annexin A1 binding partner to be bound to a matrix or other solid support.

In yet another embodiment, the invention provides methods for identifying agents (e.g., fusion proteins, polypeptides, peptidomimetics, prodrugs, receptors, binding agents, binding partners, antibodies, small molecules or other drugs, or ribozymes) which alter (e.g., increase or decrease) the activity of an annexin A1 binding partner, as described herein. For example, such agents can be agents which have a stimulatory or inhibitory effect on, for example, the activity of an annexin A1 binding partner; which change (e.g., enhance or inhibit) the ability of the annexin A1 binding partners (e.g., receptors or other binding agents) to interact with annexin A1 or an annexin A1 derivative; or which alter posttranslational processing of the annexin A1 binding partner (e.g., agents that alter proteolytic processing to direct the annexin A1 binding partner from where it is normally synthesized to another location in the cell, such as the cell surface; agents that alter proteolytic processing such that an altered amount active annexin A1 binding partner is released from the cell, etc.).

For example, the invention provides assays for screening candidate or test agents that bind to or modulate the activity of an annexin A1 binding partner, as well as agents identifiable by the assays, using methods similar to those described above in relation to assays for screening agents that modulate activity of annexin A1 or of an annexin A1 derivative. As described above, test agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) Anticancer Drug Des., 12:145).

In one embodiment, to identify agents which alter the activity of an annexin A1 binding partner, a cell, cell lysate, or solution containing or expressing an annexin A1 binding partner can be contacted with an agent to be tested; alternatively, the annexin A1 binding partner can be contacted directly with the agent to be tested. The level (amount) of annexin A1 binding partner activity is assessed (e.g., the level (amount) of annexin A1 binding partner activity is measured, either directly or indirectly), and is compared with the level of activity in a control (i.e., the level of activity of the annexin A1 binding partner or fragment or derivative thereof in the absence of the agent to be tested). If the level of the activity in the presence of the agent differs, by an amount that is statistically significant, from the level of the activity in the absence of the agent, then the agent is an agent that alters the activity of the annexin A1 binding partner. An increase in the level of annexin A1 binding partner activity relative to a control, indicates that the agent is an agent that enhances (is an agonist of) annexin A1 binding partner activity. Similarly, a decrease in the level of annexin A1 binding partner activity relative to a control, indicates that the agent is an agent that inhibits (is an antagonist of) annexin A1 binding partner activity. In another embodiment, the level of activity of an annexin A1 binding partner or derivative or fragment thereof in the presence of the agent to be tested, is compared with a control level that has previously been established. A level of the activity in the presence of the agent that differs from the control level by an amount that is statistically significant indicates that the agent alters annexin A1 binding partner activity.

This invention further pertains to novel agents identified by the above-described screening assays. Accordingly, it is within the scope of this invention to further use an agent identified as described herein in an appropriate animal model. For example, an agent identified as described herein (e.g., a test agent that is a modulating agent, an antisense nucleic acid molecule, a specific antibody, or a polypeptide-binding agent) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein. In addition, an agent identified as described herein can be used to alter activity of annexin A1 or an annexin A1 derivative, by contacting the annexin A1, annexin A1 derivative, or the gene or nucleic acid encoding the annexin A1 or annexin A1 derivative (or contacting a cell comprising the annexin A1, annexin A1 derivative, or the gene or nucleic acid encoding the annexin A1 or annexin A1 derivative) with the agent identified as described herein.

Screening Assays for Annexin A1 Binding Partners

In another embodiment, the invention provides methods for identifying agents (e.g., fusion proteins, polypeptides, peptidomimetics, prodrugs, receptors, binding agents, binding partners, antibodies, small molecules or other drugs, or ribozymes) which bind to annexin A1 or an annexin A1 derivative as described herein, or which otherwise interact with annexin A1 or an annexin A1 derivative. Binding partners can be used, for example, as targeting agents (e.g., in the methods described herein).

In one embodiment, the invention provides assays for screening candidate or test agents that bind annexin A1 or an annexin A1 derivative, as well as agents identifiable by the assays. Test agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) Anticancer Drug Des., 12:145). The National Institutes of Health also has libraries of compounds available for screening using such methods. Libraries of chemical compounds can also be assessed. Libraries of phage displaying peptides or antibodies or there derivatives can also be screened, as can libraries having viruses, nanoparticles or proteins engineered to display different peptides.

In one embodiment, to identify agents which bind to annexin A1 or an annexin A1 derivative, a cell, cell lysate, or solution containing or expressing annexin A1 or an annexin A1 derivative, can be contacted with an agent to be tested; alternatively, the polypeptide can be contacted directly with the agent to be tested. The level (amount) of binding to annexin A1 or the annexin A1 derivative is assessed (e.g., the level (amount) of activity is measured, either directly or indirectly). In another embodiment of the invention, yeast two-hybrid assays can be used to identify polypeptides that bind to annexin A1 or an annexin A1 derivative. For example, a yeast two-hybrid system such as that described by Fields and Song (Fields, S. and Song, O., Nature 340:245-246 (1989)) can be used to identify polypeptides that interact with annexin A1 or an annexin A1 derivative. In such a yeast two-hybrid system, vectors are constructed based on the flexibility of a transcription factor which has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used which includes a nucleic acid encoding a DNA binding domain and also annexin A1 or an annexin A1 derivative, and a second vector is used which includes a nucleic acid encoding a transcription activation domain and also a nucleic acid encoding a polypeptide which potentially may interact with annexin A1 or an annexin A1 derivative (e.g., an annexin A1 binding partner or receptor). Incubation of yeast containing the first vector and the second vector under appropriate conditions (e.g., mating conditions such as used in the Matchmaker™ system from Clontech) allows identification of colonies which express the markers of interest. These colonies can be examined to identify the polypeptide(s) which interact with the annexin A1 or annexin A1 derivative.

In another embodiment of the invention, libraries of small molecules can be screened to assess for molecules which bind to annexin A1 or an annexin A1 derivative. There are numerous approaches to screening for small molecule agents that bind to annexin A1 or to an annexin A1 derivative. A variety of assay formats will suffice and, in light of the present disclosure, those not expressly described herein will nevertheless be comprehended by one of ordinary skill in the art. Agents to be tested for their ability to bind to annexin A1 or to an annexin A1 derivative can be produced, for example, by bacteria, yeast, plants or other organisms (e.g., natural products), produced chemically (e.g., small molecules, including peptidomimetics), or produced recombinantly. Test agents contemplated by the present invention include non-peptidyl organic molecules, peptides, polypeptides, peptidomimetics, sugars, hormones, and nucleic acid molecules (such as nucleic acid aptamers). In a preferred embodiment, the test agent is a small organic molecule having a molecular weight of less than about 2,500 daltons.

The test agents can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target.

Antibodies of the Invention

In another aspect, the invention provides antibodies to annexin A1, that can be used, for example, in the methods of the invention. The term "antibody" is described above. The invention provides polyclonal and monoclonal antibodies that bind to a annexin A1 or a derivative of annexin A1. The term "monoclonal antibody" or "monoclonal antibody composition", as used herein, refers to a population of antibody molecules that contain only one species of an antigen binding site capable of immunoreacting with a particular epitope of annexin A1 or a derivative of annexin A1.

Polyclonal antibodies can be prepared as described above by immunizing a suitable subject with a desired immunogen, e.g., annexin A1 or derivative thereof. The antibody titer in the immunized subject can be monitored over time by standard techniques, such as with an enzyme linked immunosorbent assay (ELISA) using immobilized polypeptide. If desired, the antibody molecules directed against annexin A1 can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) Nature, 256:495-497, the human B cell hybridoma technique (Kozbor et al. (1983) Immunol. Today, 4:72), the EBV-hybridoma technique (Cole et al. (1985), Monoclonal Antibodies and Cancer Therapy, Alan R. Liss, Inc., pp. 77-96) or trioma techniques. The technology for producing hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to annexin A1 (see, e.g., Current Protocols in Immunology, supra; Galfre et al. (1977) Nature, 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387-402. Moreover, the ordinarily skilled worker will appreciate that there are many variations of such methods that also would be useful.

Alternative to preparing monoclonal antibody-secreting hybridomas, a monoclonal antibody to annexin A1 can be identified and isolated by screening a recombinant combinatorial immunoglobulin library (e.g., an antibody phage display library) with annexin A1 or a derivative of annexin A1, to thereby isolate immunoglobulin library members that bind to annexin A1. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology, 9:1370-1372; Hay et al. (1992) Hum. Antibod. Hybridomas, 3:81-85; Huse et al. (1989) Science, 246:1275-1281; Griffiths et al. (1993) EMBO J., 12:725-734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used in the methods of the invention. For example, an antibody specific for annexin A1 can be used in the methods of the invention to image a tumor or neoplasm, in order to evaluate the abundance and location of neoplasm. Antibodies can also be used diagnostically to, for example, determine the efficacy of a given treatment regimen, by imaging before and after the treatment regimen, as described above.

Use of Other Annexins

While the present invention has been exemplified by the use of annexin A1, the methods described herein can be applied in a similar manner to other annexins. Annexins, have several characteristics in common, including being cytosolic proteins that can bind lipid membranes in a calcium-dependent manner (Gerke, V., and Moss, S. E., Physiol Rev 2002; 82:331-71) and commonly existing bound at the inner leaflet of the bilayer (Gerke, V. and Moss, S. E. (2002) Physiol Rev 82, 331-71). Other annexins can be similarly used as targets of annexin therapeutic agents; as targets for imaging, either in vivo or in vitro; for diagnostics; and also for assessing treatment efficacy or prognosis of disease. Like annexin A1, other annexins can also move to and across membranes including the plasma membrane to become exposed and thus accessible to a wide variety of agents, including agents previously unable to enter cells. In certain embodiments, annexin A2 or annexin A8 are used in a manner similar to annexin A1 as described herein. For example, agents (e.g., imaging agents, therapeutic agents) can be delivered to, into and/or across vascular endothelium in a neoplasm-specific manner by contacting the luminal surface of vasculature, or caveolae of vasculature, with an agent that specifically binds to the annexin (or to a derivative of the annexin), or to a specific binding partner of the annexin (or to a specific binding partner of a derivative of the annexin). In certain embodiments, for example, the targeting agent component of an imaging agent or a therapeutic agent can be an agent that specifically binds the annexin. Additional information regarding use of other proteins, including other annexins, for neoplasm-specific delivery of agents is described in greater detail in Ser. No. 60/576,192, filed Jun. 2, 2004, entitled, "TUMOR-SPECIFIC IMAGING AND THERAPEUTIC AGENTS TARGETING PROTEINS EXPRESSED ON TUMOR ENDOTHELIAL CELL SURFACE", and Ser. No. 11/143,919, filed on even date herewith, entitled, "IMAGING AND THERAPEUTIC AGENTS TARGETING PROTEINS EXPRESSED ON ENDOTHELIAL CELL SURFACE". The teachings of which are incorporated herein by reference in their entirety.

The invention is further illustrated by the following Examples, which is not intended to be limiting in any way.

EXAMPLES

The proteomic mapping of endothelium and its caveolae, as described herein, reveals that solid tumors induce antibody accessible translocation of AnnA1 in caveolae of the neovasculature. Targeting tumor endothelial caveolae via AnnA1 permits specific delivery to, treatment of, and imaging of, solid tumors in vivo.

Example 1

Materials and Methods

Materials: Antibodies were obtained: AnnA1, AnnA3, AnnA5, AnnA7 AnnA8, caveolin-1, E-cadherin, and VE-Cadherin from Santa Cruz Biotechnology (Santa Cruz, Calif.); AnnA2, AnnA4, and AnnA6 were from BD Biosciences (San Diego, Calif.); -actin was from Sigma (Saint Louis, Mo.); VEGF R2 was from Zymed Lab, Inc. (San Francisco, Calif.); mouse IgGs were from Southern Biotech (Birmingham, Ala.); VEGF receptor 1 was a kind gift of Dr. D. Sanger, Beth Israel Deaconess Medical Center (Boston Mass.); galectin 1 was a kind gift of Dr. M. Huflejt, Sidney Kimmel Cancer Center (San Diego, Calif.); podocalyxin was produced in house.

Cloning of AnnA1 cDNA and antibody production: Monoclonal antibodies were generated by standard somatic cell hybridization using purified recombinant AnnA1 as an immunogen and were screened by ELISA with P adsorbed onto 96-well trays.

Isolation of luminal endothelial cell plasma membranes and caveolae: The luminal endothelial cell plasma membranes and their caveolae were isolated directly from tissue as described (Schnitzer, J. E., McIntosh, D. P., Dvorak, A. M., Liu, J. and Oh, P. (1995) Separation of caveolae from associated microdomains of GPI-anchored proteins. Science 269, 1435-9; Oh, P. and Schnitzer, J. E. Isolation and subfractionation of plasma membranes to purify caveolae separately from glycosyl-phosphatidylinositol-anchored protein microdomain. in Cell Biology: A Laboratory Handbook, Vol. 2 (ed. Celis, J.) 34-36 (Academic Press, Orlando, 1998) Schnitzer, J. E. et al. J. Biol Chem. 270:14399-14404 (1995)).

Tumor models: Female Fisher rats (100-150 gms) were injected via the tail vein with a cell suspension of 13762 breast adenocarcinoma cells to give ample, well circumscribed, and highly vascularized tumors in the lung. To create a maximum density of tumor lesions of 3-8 mm in diameter that are clearly visible in the lungs, 5×105 13762 cells were injected 14-15 days prior to perfusion and isolation of tumor-bearing lung P. To obtain a few well-circumscribed tumors of 3-6 mm in diameter, 1×105 cells were injected 21 days prior to performing the imaging experiments. A subcutaneous (s.c.) breast tumor model in mice was generated by injecting 1.8× 107 MDAMB435 cells s.c. on the backs of nude mice and allowed to grow for 12 days prior to imaging studies.

Mass spectrometric analysis: AnnA1 was excised from proteins isolated from P and V; the proteins were separated by 1D or 2D gel electrophoresis. In addition, AnnA1 was immunoprecipitated from P using AnnA1 mAb as described (Oh, P. and Schnitzer, J. E. (2001) Segregation of heterotrimeric G proteins in cell surface microdomains: Gq binds caveolin to concentrate in caveolae whereas Gi and Gs target lipid rafts by default. Mol. Biol. Cell 12, 685-698). The immunoprecipitated material was analyzed by SDS-PAGE and the single 34 kDa band (corresponding to AnnA1 by Western analysis) was excised from the gel. The excised gel bands or spots were subjected to in-gel trypsin digest prior to MS analysis. The complex peptide mixture was separated using a microcolumn packed with reversed phase C-18 material and connected to an HPLC solvent delivery system then eluted over 60 minutes via a binary gradient directly into the electrospray ion trap mass spectrometer (LCQ Deca, ThermoFinnigan, San Jose, Calif.), which provides recorded mass spectra between m/z 400 and 1600. Automated analysis of ion spectra was performed using SEQUEST software which performs an extensive comparison of acquired MS/MS spectra with the spectra of known proteins in available public databases to identify known proteins.

Tissue staining: Frozen rat tissues were cut (5 μm) on a Microm HM505E cryomicrotome. Sections were fixed with neutral buffered formalin for 5 min at room temperature then incubated for one hour at room temperature in blocking solution (5% FBS, 0.1% Tween 20 in PBS). After a 2-hour incubation at room temperature in primary antibodies (diluted in blocking solution) the sections were washed then treated with the appropriate biotin-conjugated secondary antibody (KPL Laboratories, Gaithersburg, Md.) for 1 hour at room temperature, washed again then treated with a streptavidin-conjugated horseradish peroxidase (KPL Laboratories, Gaithersburg, Md.) for 1 hour at room temperature. Immune complexes were detected using a Liquid DAB staining kit from BioGenex (San Ramon, Calif.). Formalin-fixed, paraffin-embedded sections (5 μm) were cut on a Microm HM340E microtome. Antigen retrieval was performed using and acid citrate buffer following standard procedures. After the sections were washed in water to remove the citrate buffer, they were blocked and immunostained as above.

Animal use: Animal experiments were in accordance with federal guidelines following review and approval by the Sidney Kimmel Cancer Center animal care and use committee.

Gamma scintigraphic imaging and biodistribution analysis: Monoclonal antibodies were isolated using GammaBind Plus Sepharose (Amersham, Piscataway, N.J.) and conjugated to 125I using Iodogen as described (McIntosh, D. P., Tan, X.-Y., Oh, P. and Schnitzer, J. E. (2002) Targeting endothelium and its dynamic caveolae for tissue-specific transcytosis in vivo: A pathway to overcome cell barriers to drug and gene delivery. Proc. Natl. Acad. Sci. USA 99, 1996-2001). Biodistribution analysis was performed as described (id.). Imaging was performed using an A-SPECT (McElroy, D., MacDonald, L., Beekman, F., Wang, Y., Patt, B., Iwanczyk, J., Tsui, B. and Hoffman, E. (2002) Performance evaluation of A-SPECT: A high resolution desktop pinhole SPECT system for imaging small animals. IEEE Trans Nucl Sci NS 49, 2139-2147), fitted with a parallel-hole collimator. Normal and tumor-bearing female Fisher rats were anaesthetized and injected via the tail vein with 125I-labeled monoclonal antibody (5 μg IgG; 10 μCi/μg) before being subjected to planar gamma scintigraphic imaging captured over 10 min. After whole body imaging, in some cases, the lungs were excised for planar imaging captured over 10 min ex vivo.

Example 2

Results and Discussion

Past work has mapped and characterized extensively the molecular architecture and function of the cell surface, especially its caveolae, in normal vascular endothelium, primarily in rat lung tissue (Schnitzer, J. E. and Oh, P. (1994) A1bondin-mediated capillary permeability to albumin. Differential role of receptors in endothelial transcytosis and endocytosis of native and modified albumins. J Biol Chem 269, 6072-82; Schnitzer, J. E., Oh, P., Pinney, E. and Allard, J. (1994) Filipin-sensitive caveolae-mediated transport in endothelium: reduced transcytosis, scavenger endocytosis, and capillary permeability of select macromolecules. J Cell Biol 127, 1217-32; Schnitzer, J. E., McIntosh, D. P., Dvorak, A. M., Liu, J. and Oh, P. (1995) Separation of caveolae from associated microdomains of GPI-anchored proteins. Science 269, 1435-9; Schnitzer, J. E., Oh, P. and McIntosh, D. P. (1996) Role of GTP hydrolysis in fission of caveolae directly from plasma membranes [publisher's erratum appears in Science 1996 Nov. 15;274(5290):1069]. Science 274, 239-42; Schnitzer, J. E., Liu, J. and Oh, P. (1995) Endothelial caveolae have the molecular transport machinery for vesicle budding, docking, and fusion including VAMP, NSF, SNAP, annexins, and GTPases. J Biol Chem 270, 14399-404; Schnitzer, J. E., Allard, J. and Oh, P. (1995) NEM inhibits transcytosis, endocytosis, and capillary permeability: implication of caveolae fusion in endothelia. Am J Physiol 268, H48-55; McIntosh, D. P. and Schnitzer, J. E. (1999) Caveolae require intact VAMP for targeted transport in vascular endothelium. Am J Physiol 277, H2222-32.).

Using subcellular fractionation to isolate caveolae (V) and/ or silica coated luminal endothelial cell plasma membranes (P) from tissue as previously described (Schnitzer, J. E., McIntosh, D. P., Dvorak, A. M., Liu, J. and Oh, P. (1995) Separation of caveolae from associated microdomains of GPI-anchored proteins. Science 269, 1435-9; Schnitzer, J. E., Oh, P. and McIntosh, D. P. (1996) Role of GTP hydrolysis in fission of caveolae directly from plasma membranes [publisher's erratum appears in Science 1996 Nov. 15 ;274(5290): 1069]. Science 274, 239-42; Schnitzer, J. E., Liu, J. and Oh, P. (1995) Endothelial caveolae have the molecular transport machinery for vesicle budding, docking, and fusion including VAMP, NSF, SNAP, annexins, and GTPases. J Biol Chem 270, 14399-404; Schnitzer, J. E., Allard, J. and Oh, P. (1995) NEM inhibits transcytosis, endocytosis, and capillary permeability: implication of caveolae fusion in endothelia. Am J Physiol 268, H48-55; McIntosh, D. P. and Schnitzer, J. E. (1999) Caveolae require intact VAMP for targeted transport in vascular endothelium. Am J Physiol 277, H2222-32; Oh, P. and Schnitzer, J. E. Isolation and subfractionation of plasma membranes to purify caveolae separately from glycosylphosphatidylinositol-anchored protein microdomain. In Cell Biology: A Laboratory Handbook, Vol. 2 (ed. Celis, J.) 34-36 (Academic Press, Orlando, 1998)), the possible equivalence of normal rat lung endothelial caveolae to caveolae from tumor endothelia and even from human samples was examined. Normal rat lung endothelial caveolae contained annexin A2 (AnnA2) but not annexin A1 (AnnA1), which was previously thought to be restricted in expression to neuronal and select secretory cells (McKanna, J. A. and Zhang, M. Z. (1997) Immunohistochemical localization of lipocortin 1 in rat brain is sensitive to pH, freezing, and dehydration. J Histochem Cytochem 45, 527-38; Savchenko, V. L., McKanna, J. A., Nikonenko, I. R. and Skibo, G. G. (2000) Microglia and astrocytes in the adult rat brain: comparative immunocytochemical analysis demonstrates the efficacy of lipocortin 1 immunoreactivity. Neuroscience 96, 195-203; Naciff, J. M., Kaetzel, M. A., Behbehani, M. M. and Dedman, J. R. (1996) Differential expression of annexins I-VI in the rat dorsal root ganglia and spinal cord. J Comp Neurol 368, 356-70; Eberhard, D. A., Brown, M. D. and VandenBerg, S. R. (1994) Alterations of annexin expression in pathological neuronal and glial reactions. Immunohistochemical localization of annexins I, II (p36 and p11 subunits), IV, and VI in the human hippocampus. Am J Pathol 145, 640-9).

The analysis described herein confirmed the expression of AnnA2 in caveolae, this time from various human tissues, including tumors. As expected, AnnA1 was not detected in caveolae from normal human tissues but, surprisingly, it was detected readily by affinity-purified polyclonal antibodies (C19) as a 34 kDa band in caveolae isolated from multiple human solid tumors (kidney, liver, lung, brain, breast, and prostate; see, for example, U.S. Pat. No. 6,737,516 for methods to isolate human caveolae).

These results were corroborated by proteomic analysis of caveolae isolated from multiple rat tumor models (induced by fibrosarcoma (MR7) and mammary adenocarcinoma (13762 and MTLn3) cells injected into the rat tail vein). Mass spectrometric (MS) analysis of tryptic peptides from a 34 kDa protein band readily apparent in SDS-PAGE gels of lung tumor caveolae but not in normal lung caveolae provided multiple peptide sequences that identified the protein as AnnA1. So far, 30 peptides providing ~55% sequence coverage for AnnA1 have been identified by performing MS analysis on multiple samples: I) as the excised 34 kDa band found in tumor but not normal caveolae by 1-D gel analysis; ii) as spots on 2-D gels from caveolae isolated from tumor but not normal tissue; iii) in AnnA1 immunoprecipates from P isolated from tumors; and iv) MudPIT analysis of P and V isolated from rat tumors.

Western analysis of tissue subfractions from these rat lung tumor models using AnnA1 polyclonal antibodies also revealed a single 34 kDa band enriched in caveolae from the tumor-bearing but not normal lungs, thereby confirming AnnA1 expression concentrated in the isolated caveolae and apparently induced on the blood vessel cell surface by the tumors. The caveolae structural protein, caveolin-1, and AnnA2 were enriched in the V fraction as reported (Schnitzer, J. E., McIntosh, D. P., Dvorak, A. M., Liu, J. and Oh, P. (1995) Separation of caveolae from associated microdomains of GPI-anchored proteins. Science 269, 1435-9; Oh, P. and Schnitzer, J. E. (1999) Immunoisolation of caveolae with high affinity antibody binding to the oligomeric caveolin cage. Toward understanding the basis of purification [published erratum appears in J Biol Chem 1999 Oct. 8 ;274(41): 29582]. J Biol Chem 274, 23144-54). In contrast, there was no detection of Gal-1 and β-COP, known to be expressed elsewhere in tumor cells and Golgi/endosomes, respectively (Perillo, N. L., Marcus, M. E. and Baum, L. G. (1998) Galectins: versatile modulators of cell adhesion, cell proliferation, and cell death. J Mol Med 76, 402-12; Griffiths, G., Pepperkok, R., Locker, J. K. and Kreis, T. E. (1995) Immunocytochemical localization of beta-COP to the ER-Golgi boundary and the TGN. J Cell Sci 108 (Pt 8), 2839-56). Also, ACE, VEGF-R1 and VEGF-R2 were enriched in the isolated luminal endothelial cell plasma membranes from both normal and tumor lungs but not the caveolae. Thus, AnnA1 appears to be induced in the endothelial cell caveolae of the neovasculature of rat and human solid tumors.

To determine whether AnnA1 is unique among the annexins in its expression on the endothelial cell surface of tumor blood vessels, Western analysis was performed on tissue homogenates (H) and P from multiple normal organs as well as tumor-bearing lungs from rats using antibodies recognizing various annexin proteins AnnA1 was readily detected enriched in P isolated from rat lung tumors but not from normal tissues. In contrast, AnnA2 was easily detected in P from normal lung, liver, kidney, and heart; annexin A5 in normal lung and brain P; and annexin A8 in normal lung P Annexins A4, A6, and A7 were even more widely distributed Annexin A3 antibodies did not give a clean enough signal to accurately assess localization.

To further assess the tumor-specificity of AnnA1 expression, various rat and human normal and tumor tissues were immunostained AnnA1 antibody stained blood vessels of human prostate, liver, kidney, breast, colon, brain and lung tumors but not matched normal tissues. Human metastatic tumors (colon metastasis to the lung and breast metastasis to the brain) also showed AnnA1 expression in the blood vessels. Antibodies to PECAM, a pan-endothelial marker, stained both normal and tumor blood vessels. The lack of AnnA1 expression in vascular endothelium of tissue sections of multiple normal organs has been reported previously (McKanna, J. A. and Zhang, M. Z. (1997) Immunohistochemical localization of lipocortin 1 in rat brain is sensitive to pH, freezing, and dehydration. J Histochem Cytochem 45, 527-38; Eberhard, D. A., Brown, M. D. and VandenBerg, S. R. (1994) Alterations of annexin expression in pathological neuronal and glial reactions. Immunohistochemical localization of annexins I, II (p36 and p11 subunits), IV, and VI in the human hippocampus. Am J Pathol 145, 640-9; Dreier, R., Schmid, K. W., Gerke, V. and Riehemann, K. (1998) Differential expression of annexins I, II and IV in human tissues: an immunohistochemical study. Histochem Cell Biol 110, 137-48; Ahn, S. H., Sawada, H., Ro, J. Y. and Nicolson, G. L. (1997) Differential expression of annexin I in human mammary ductal epithelial cells in normal and benign and malignant breast tissues. Clin Exp Metastasis 15, 151-6). Thus, AnnA1 expression appeared by Western analysis and tissue immunostaining to be induced in the neovasculature of both rat lung tumor models and in multiple human solid tumors.

Some of the commercially available antibodies appeared to react preferentially with the 34 kDa form of annexin A1 and gave a clean signal of expression in tumor vasculature; however, to better characterize AnnA1 expression and to test possible in vivo targeting of targeting in vivo, additional high affinity, specific probes were used. After testing commercially available AnnA1 monoclonal antibodies (mAbs), it was decided to generate a panel of mAbs recognizing AnnA1 from multiple species. Rat, mouse, and human AnnA1 cDNAs were cloned by PCR. To validate the cDNA clones, cultured cells were transfected with a mammalian expression vector containing the cDNA and tested for AnnA1 reactivity vs. non-transfected cells by Western analysis and immunofluorescence microscopy. Using these cDNAs, recombinant protein was produced from each of the three species as immunogens to generate a panel of mAbs recognizing rat, mouse, and human AnnA1.

Annexins, including AnnA1, normally are cytosolic proteins that can bind cell membranes usually at the inner leaflet of the bilayer in a calcium-dependent manner (Schnitzer, J. E. (2001) Caveolae: from basic trafficking mechanisms to targeting transcytosis for tissue-specific drug and gene delivery in vivo. Adv Drug Deliv Rev 49, 265-80). But some annexins may translocate across the lipid bilayer to remain bound to the plasma membrane on the external cell surface (Gerke, V. and Moss, S. E. (2002) Annexins: from structure to function. Physiol Rev 82, 331-71).

To test whether AnnA1 induced on the tumor endothelial cell surface is exposed to circulating antibody, AnnA1 antibodies were perfused into normal and tumor-bearing rat lungs then flushed the vasculature to remove unbound antibody AnnA1 antibody was readily detected by Western analysis in P isolated from the lungs bearing tumors but not normal lungs whereas control APP antibody was bound to normal lung P. Immunohistochemical staining of tissue sections also detected the AnnA1 antibodies bound to the vascular endothelium of tumors but not normal lungs. Thus, AnnA1 must be externalized and exposed bound on the outer leaflet of the luminal endothelial cell plasma membrane and thus readily accessible to the antibody in circulation.

To test whether the AnnA1 in caveolae is sufficiently IV-accessible and specific for tumor blood vessels to permit significant tumor targeting in vivo, biodistribution analysis was performed after injecting radio-iodinated mAbs to AnnA1, AnnA2, and AnnA4 which, as shown above, exhibit tumor specific, restricted, and wide expression, respectively, in rat tissue. After 60 min, multiple organs, including the whole lungs with tumors, were excised, weighed, and counted for radioactivity. The AnnA1 antibody accumulated significantly and specifically in the tumor-bearing lungs at levels of about 15% of the injected dose (ID) per gram of tumor-bearing lung compared to other organs at <1% ID/g tissue. In animals without tumors, AnnA1 antibody showed no specific targeting of lung with <1% of ID/g detected AnnA2 showed some evidence of IV-accessible exposure in rat lung tumors resulting in moderate yet significant accumulation in lung tumors with 4.22% ID/g in tumor lungs compared to quite low accumulation in normal tissues (<1% ID/g). The AnnA4 antibodies exhibited no specific tumor targeting with most of the antibodies remaining in the blood, consistent with the expected intracellular distribution of this protein. In time course studies, significant accumulation of AnnA1 antibody was observed at 30 min (7% ID/g) reaching a maximum by two hours (17% ID/g) which was maintained for at least 24 hours. When the tumors were dissected away from normal lung tissue and counted for radioactivity, the tumor targeting was even more striking with an accumulation 11.5% ID/g of tumor at 30 min reaching a maximum of 33% ID/g of tumor at 2 hours. These data indicate that AnnA1 (and possibly to a minor degree AnnA2 but not AnnA4) in tumor endothelial cell caveolae is exposed on the outside of the cell and is readily accessible by IV injection for tumor-selective delivery in vivo.

Given the biodistribution analysis showing promising tumor targeting, tumor targeting was further examined in vivo by high resolution pinhole micro-SPECT imaging of rats bearing lung tumors. 125I-AnnA1 mAbs were injected into the tail vein of sedated rats and images captured 4 hours later showed several distinct foci of increased radioactivity ("hot spots") of different sizes in the lung. This was especially evident when lungs with multiple tumors were imaged ex vivo so that the tumors could be seen to overlap directly with the hot spots. A 3D movie of the SPECT imagines illustrated further the targeting. Moreover, 125I-AnnA1 mAb accumulation in tumors was specific because co-injection of a 30-fold excess of unlabeled AnnA1 mAbs (but not excess non-targeting unlabeled IgG) competed with tumor AnnA1 mAb binding. 125I-AnnA1 mAbs were also injected into the tail vein of mice bearing a subcutaneous breast tumor model and imaged the mice 3 hours later. Clear specific labeling of the externally apparent tumors occurred. Non-targeting 125I-labeled IgGs did not target any specific tissue with the signal reflecting the customary low level diffuse "blood pool" image. Thus, SPECT imaging showed specific accumulation of 125I-AnnA1 mAbs in the tumor but not elsewhere, indicating AnnA1 mAbs did specifically target multiple tumors in rat and mouse models.

Antibodies targeting caveolae can be transported across the endothelial cell barrier into the tissue parenchyma (McIntosh, D. P., Tan, X.-Y., Oh, P. and Schnitzer, J. E. (2002) Targeting endothelium and its dynamic caveolae for tissue-specific transcytosis in vivo: A pathway to overcome cell barriers to drug and gene delivery. Proc. Natl. Acad. Sci. USA 99, 1996-2001). To assess possible penetration of AnnA1 antibodies into tumors after specific tumor endothelial cell surface binding, AnnA1 mAbs were injected into the tail veins of rats bearing metastatic breast tumors growing in their lungs. After 4 hours, the lungs bearing lung tumors were flushed, excised, sectioned and stained for the presence of AnnA1 mAb using HRP-conjugated secondary antibodies AnnA1 mAb binding was detected on the tumor but not normal lung endothelium confirming further the specific binding of AnnA1 mAbs at the endothelial cell surface in the microvasculature of tumors. In addition, a "halo" of brown signal was consistently observed emanating from the blood vessels into the tissue, indicating penetration of the AnnA1 mAbs into the tumor tissue adjacent to the microvasculature. This antibody penetration into the tumor interstitium was not readily detected 1 hr post-injection. Thus, mAbs recognizing AnnA1 specifically target and traverse the blood vessels in multiple tumor types in rat and mouse models to gain access to the tumor interstitium within 4 hours.

While performing 125I-AnnA1 antibody biodistribution and imaging experiments, it was noticed that the tumor-bearing rats injected IV with 125I-AnnA1 antibodies were surviving longer than the non-injected animals and also the animals injected with non-targeting control antibodies (125I-IgG). Histological tissue examination of sections of tumor-bearing lungs from 125I-AnnA1 antibody-treated vs. control animals three days post-injection revealed much more extensive tumor necrosis in the treated animals. The adjacent normal lung tissue as well as other major organs of the body appeared undamaged. The tumors in the 125I-AnnA1 antibody-treated animals were significantly smaller (by ~50% in diameter).

Survival studies were performed. FIG. 1 shows survival plotted on a Kaplan-Meier survival curve. Female Fisher rats were injected IV with 13762 cells to induce tumors (Day 0). The Kaplan-Meier survival curve comparing the survival of tumor-bearing rats injected 15 days after tumor cell inoculation with 125I-AnnA1 antibodies (50 g, 10 Ci/ g; solid line; n=10) vs. control non-targeting 125I-IgG (dashed line; n=10) vs. untreated animals (dotted line; n=3). FIG. 1 shows survival over 60 days plotted on a Kaplan-Meier survival curve. Significantly increased survival of the tumor-bearing rats was observed, with 80% of the animals surviving 8 days or longer after injection compared to 100% mortality in the control rats by 7 days post-injection. The rats injected with 125I-AnnA1 antibodies were imaged to show both the expected distribution of rat lung tumors and 125I-AnnA1 antibody accumulation in the tumors.

Figure 2:
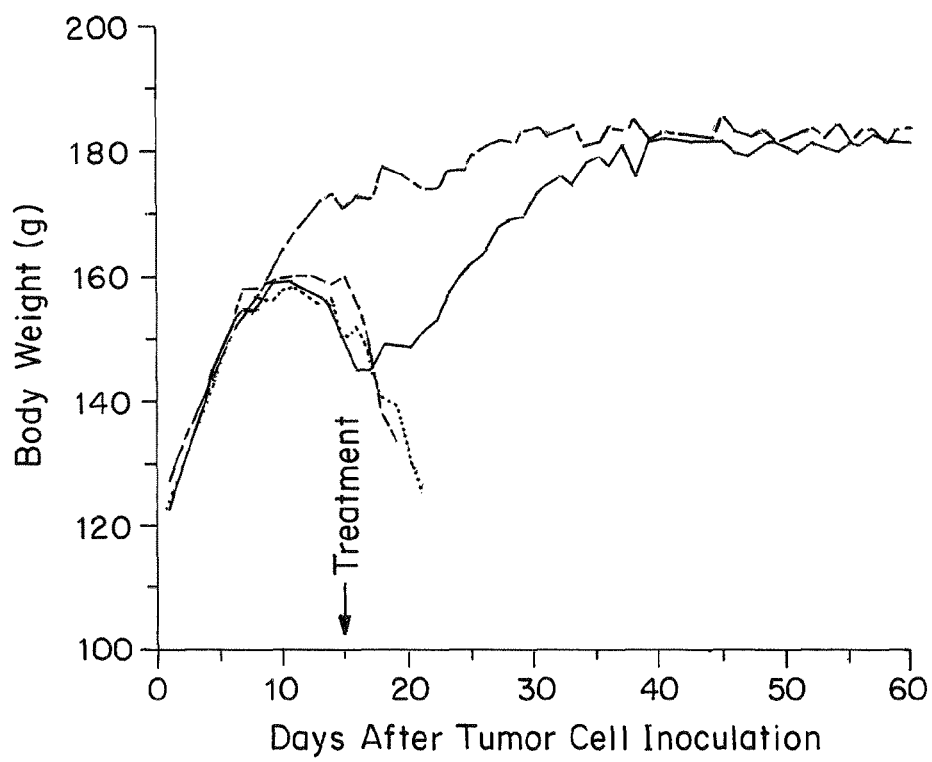
FIG. 2 depicts body weight of the animals in comparison to treatment. Body weight deviated from normal in all animals after inoculation with tumor cells. Whereas untreated rats and rats injected with control antibodies continued to lose body weight, rats treated with 125I-AnnA1 antibodies stopped losing weight within 3 days post-treatment and then gained weight to reach a normal body weight 20 days after treatment.

In addition, the body weight of all the rats began to deviate from the normal weight at 8 days and actually to decline at 10 days after IV inoculation with the tumor cells. Both untreated rats and rats injected with 125I-labeled non-targeting control antibodies continued to lose body weight until their death at which time they weighed 25-30% less than normal. In contrast, rats treated with 125I-AnnA1 antibodies stopped losing weight within 3 days post-treatment and then gained weight to reach a normal body weight 20 days after treatment (FIG. 2; solid line, tumour-bearing rats treated with 125I-AnnaA1 antibodies; dashed line, tumour-bearing rats treated with control 125I-IgG; dotted line, untreated tumour-bearing animals; dotted and dashed line, untreated normal rats. N=3; maximum standard deviation <10 grams for each weight plotted). This drastic increase in survival was surprising because the animals were within as little as 2 days of death at the time of treatment so that they may lack sufficient time to benefit from any widespread radiation damage to the endothelium and tumor cells. If the rat was able to survive the first week after the injection, by which time all control animals have died, the survival rate approached 90%. The one rat that died after two weeks had to be euthanized because of a leg tumor and large tail tumor that developed at the injection site. Thus, a single injection of 125I-AnnA1 antibody did in fact appear to be safe as well as cause significant remission even in advanced disease.

While generating the recombinant AnnA1 (rAnnA1) and our new AnnA1 mAbs, a molecular weight of 38 kDa was observed for rAnnA1 by SDS-PAGE, consistent with the molecular weight of 37 kDa from primary sequence data and as reported in the literature (Chapman, L., Nishimura, A., Buckingham, J. C., Morris, J. F. and Christian, H. C. (2002) Externalization of annexin I from a folliculo-stellate-like cell line. Endocrinology 143, 4330-8). When subfractions of tumor-bearing lungs were analyzed, the AnnA1 mAb detected a 38 kDa band in normal H consistent with size observed using rAnnA1. However, Western analysis of tumor lung P revealed that in tissue, rather than migrate at the expected size of 38 kDa, the AnnA1 band appeared to migrate at ~34 kDa. The 34 kDa band is indeed AnnA1 because: I) MS analysis identified AnnA1 in SDS-PAGE gel slices cut at 34 kDa and 38 kDa; ii) immunoprecipitation of tumor lung homogenates using AnnA1 mAbs also yielded a 34 kDa and a 38 kDa bands that were identified by MS analysis as AnnA1. A truncated 32-34 kDa form of AnnA1 has been reported (Taylor, A. D., Cowell, A. M., Flower, J. and Buckingham, J. C. (1993) Lipocortin 1 mediates an early inhibitory action of glucocorticoids on the secretion of ACTH by the rat anterior pituitary gland in vitro. Neuroendocrinology 58, 430-9; Philip, J. G., Flower, R. J. and Buckingham, J. C. (1997) Glucocorticoids modulate the cellular disposition of lipocortin 1 in the rat brain in vivo and in vitro. Neuroreport 8, 1871-6; Croxtall, J. D. and Flower, R. J. (1992) Lipocortin 1 mediates dexamethasone-induced growth arrest of the A549 lung adenocarcinoma cell line. Proc Natl Acad Sci U S A 89, 3571-5; Taylor, A. D., Christian, H. C., Morris, J. F., Flower, R. J. and Buckingham, J. C. (1997) An antisense oligodeoxynucleotide to lipocortin 1 reverses the inhibitory actions of dexamethasone on the release of adrenocorticotropin from rat pituitary tissue in vitro. Endocrinology 138, 2909-18). The data herein indicate that it is this smaller form that resides specifically in the caveolae of lung tumor endothelial cells. Interestingly, the C19 antibody appears to prefer the 34 kDa form of AnnA1.

To determine whether the 34 kDa form of AnnA1 is indeed the form of the protein that is exposed to the blood stream on the surface of endothelial cells, biotinylated AnnA1 mAb was injected IV into rats bearing lung tumors and allowed to circulate for 2 hours before chemical crosslinking via perfusion of DTSSP into the pulmonary artery. After isolation of tumor P, the cell surface AnnA1 was precipitated using streptavidin magnetic beads. When the AnnA1 mAb immunoprecipate was separated under non-reducing conditions, an ~180 kDa band is recognized by both anti-IgG and AnnA1 antibodies. Under reduced conditions, the anti-IgG antibody detects two bands of 25 kDa and 50 kDa corresponding to the immunoglobulin light and heavy chain, respectively, whereas the AnnA1 antibody recognizes primarily a single band at 34 kDa. To confirm the source of the immunoprecipitated AnnA1 antibody-reactive band, the SDS-PAGE gel was Coomassie stained to visualize all proteins present in the sample. MS analysis of tryptic peptides derived from this band confirms its identity as AnnA1 (data not shown). Thus, the 34 kDa form of AnnA1 is indeed the predominant form of AnnA1 that is externalized on the endothelial cell surface in caveolae.

The discovery of AnnA1, primarily its 34 kDa cleaved form, as an accessible vascular tumor target has been achieved using a combination of proteomic and molecular imaging tools, including tissue subcellular fractionation, gel electrophoresis, mass spectrometric analysis, tissue immunostaining, and SPECT imaging.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of delivering an agent into and/or across neovascular endothelium by active transport mediated by caveolae in vivo in a neoplasm-specific manner, comprising contacting the luminal endothelial surface and/or caveolae of neovasculature with said agent that comprises an antibody or antibody fragment that specifically binds to annexin A1 and results in concentration of the agent in a neoplasm in an amount greater than would occur by passive transport.

2. A method of assessing an individual for the presence or absence of a neoplasm, comprising:
   a) delivering an agent of interest into and/or across neovascular endothelium by active transport mediated by caveolae in vivo in a neoplasm-specific manner to the individual wherein the agent of interest comprises an imaging agent component and a targeting agent component, wherein the targeting agent component comprises an antibody or antibody fragment that specifically binds to annexin A1 and results in concentration of the agent in the neoplasm in an amount greater than would occur by passive transport,
   b) assessing the individual for the presence or absence of the concentration of the agent of interest,
wherein the presence of the concentration of the agent of interest is indicative of the presence of a neoplasm.

3. A method of delivering an imaging agent into and/or across neovascular endothelium by active transport mediated by caveolae in vivo in a neoplasm-specific manner, comprising contacting the luminal surface and/or caveolae of neovasculature with an agent of interest that comprises an imaging agent component and a targeting agent component, wherein the targeting agent component comprises an antibody or antibody fragment that specifically binds to annexin A1 and results in concentration of the agent in a neoplasm in an amount greater than would occur by passive transport.

4. A method of delivering an agent into and/or across neovascular endothelium by active transport mediated by caveolae in vivo in a neoplasm-specific manner, comprising contacting the luminal endothelial surface and/or caveolae of neovasculature with an agent that comprises an antibody or antibody fragment that specifically binds to a derivative of annexin A1, wherein said derivative is a truncated annexin A1 that has a molecular weight of 32-34 kDA and is isolatable from caveolae of tumor tissue, but not from caveolae of normal tissue, and results in concentration of the agent in a neoplasm in an amount greater than would occur by passive transport.

5. A method of assessing an individual for the presence or absence of a neoplasm, comprising:
   a) delivering an agent of interest into and/or across neovascular endothelium by active transport mediated by caveolae in vivo in a neoplasm-specific manner to the individual, wherein the agent of interest comprises an imaging agent component and a targeting agent component, wherein the targeting agent component comprises an antibody or antibody fragment that specifically binds to a derivative of annexin A1, wherein the derivative is a truncated annexin A1 that has a molecular weight of 32-34 kDA and is isolatable from caveolae of tumor tissue, but not from caveolae of normal tissue and results in concentration of the agent in a neoplasm in an amount greater than would occur by passive transport, and
   b) assessing the individual for the presence or absence of the concentration of the agent of interest,
wherein the presence of the concentration of the agent of interest is indicative of the presence of a neoplasm.

6. A method of delivering an imaging agent into and/or across neovascular endothelium by active transport mediated by caveolae in vivo in a neoplasm-specific manner, comprising contacting the luminal surface and/or caveolae of neovasculature with an agent of interest that comprises an imaging agent component and a targeting agent component, wherein the targeting agent component comprises an antibody or antibody fragment that specifically binds to a derivative of annexin A1, wherein the derivative of annexin A1 is a truncated annexin A1 that has a molecular weight of 32-34 kDA and is isolatable from caveolae of tumor tissue, but not from caveolae of normal tissue and results in concentration of the agent in a neoplasm in an amount greater than would occur by passive transport.

* * * * *